US012127743B2

(12) United States Patent
Xu et al.

(10) Patent No.: US 12,127,743 B2
(45) Date of Patent: Oct. 29, 2024

(54) INVERTING BRAIDED ANEURYSM IMPLANT WITH DOME FEATURE

(71) Applicant: DePuy Synthes Products, Inc., Raynham, MA (US)

(72) Inventors: Ruijiao Xu, Miami Lakes, FL (US); Lacey Gorochow, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 17/478,081

(22) Filed: Sep. 17, 2021

(65) Prior Publication Data

US 2022/0087681 A1 Mar. 24, 2022

Related U.S. Application Data

(60) Provisional application No. 63/082,013, filed on Sep. 23, 2020.

(51) Int. Cl.
*A61B 17/12* (2006.01)
*A61B 17/00* (2006.01)
*A61L 31/18* (2006.01)

(52) U.S. Cl.
CPC .... *A61B 17/12113* (2013.01); *A61B 17/1214* (2013.01); *A61B 2017/00526* (2013.01)

(58) Field of Classification Search
CPC .......... A61B 17/12113; A61B 17/1214; A61B 17/12145; A61B 17/12022;
(Continued)

(56) References Cited

U.S. PATENT DOCUMENTS

| 4,085,757 A | 4/1978 | Pevsner |
| 4,282,875 A | 4/1981 | Serbinenko et al. |

(Continued)

FOREIGN PATENT DOCUMENTS

| CA | 2395796 A1 | 7/2001 |
| CA | 2 431 594 A1 | 9/2002 |

(Continued)

OTHER PUBLICATIONS

Extended European Search Report dated Feb. 11, 2022 issued in corresponding EP Appln. No. 21 19 8510.

*Primary Examiner* — Katherine M Rodjom
*Assistant Examiner* — Lindsey R. Rivers
(74) *Attorney, Agent, or Firm* — Troutman Pepper Hamilton Sanders LLP

(57) ABSTRACT

An implant can be implanted in an aneurysm to cause thrombogenesis within the aneurysm's sac. The implant can include a braid that can extend across the aneurysm neck and anchor to aneurysm's walls at least in the proximal portion of the aneurysm sac. The implant can further include a dome feature configured to press into aneurysm walls near the aneurysm's dome and facilitate securement of the braid across the aneurysm's neck. The braid at the aneurysm's neck and the dome feature can be joined or constricted at a junction, for instance with a radiopaque band. The dome feature can include a braid, embolic coil, and/or wire frame. The braid can be inverted based on a heat-set predetermined shape, where several predetermined shapes are suitable.

19 Claims, 11 Drawing Sheets

(58) Field of Classification Search
CPC ........ A61B 17/12027; A61B 17/12031; A61B 17/12099; A61B 17/12131; A61B 17/12168; A61B 17/12172; A61B 17/1205; A61B 17/12054; A61B 17/12163; A61B 2017/1205; A61B 2017/12054; A61B 2017/12059; A61B 2017/12063; A61B 2017/12068; A61B 2017/00867

See application file for complete search history.

(56) References Cited

U.S. PATENT DOCUMENTS

| | | | |
|---|---|---|---|
| 4,517,979 A | 5/1985 | Pecenka | |
| 5,261,916 A | 11/1993 | Engelson | |
| 5,304,195 A | 4/1994 | Twyford, Jr. et al. | |
| 5,928,260 A | 7/1999 | Chin et al. | |
| 5,941,249 A | 8/1999 | Maynard | |
| 5,964,797 A | 10/1999 | Ho | |
| 6,063,100 A | 5/2000 | Diaz et al. | |
| 6,193,708 B1 | 2/2001 | Ken et al. | |
| 6,375,606 B1 | 4/2002 | Garbaldi et al. | |
| 6,379,329 B1 | 4/2002 | Naglreiter et al. | |
| 6,391,037 B1 | 5/2002 | Greenhalgh | |
| 6,454,780 B1 | 9/2002 | Wallace | |
| 6,506,204 B2 | 1/2003 | Mazzocchi | |
| 6,849,081 B2 | 2/2005 | Sepetka et al. | |
| 6,964,657 B2 | 11/2005 | Cragg et al. | |
| 6,994,711 B2 | 2/2006 | Hieshima et al. | |
| 7,377,932 B2 | 5/2008 | Mitelberg et al. | |
| 7,985,238 B2 | 7/2011 | Balgobin et al. | |
| 8,048,145 B2 | 11/2011 | Evans et al. | |
| 8,062,325 B2 | 11/2011 | Mitelberg et al. | |
| 8,523,902 B2 | 9/2013 | Heaven et al. | |
| 8,551,132 B2 | 10/2013 | Eskridge et al. | |
| 8,777,974 B2 | 7/2014 | Amplatz et al. | |
| 8,900,304 B1 | 12/2014 | Alobaid | |
| 8,974,512 B2 | 3/2015 | Aboytes et al. | |
| 8,998,947 B2 | 3/2015 | Aboytes et al. | |
| 9,055,948 B2 | 6/2015 | Jaeger et al. | |
| 9,161,758 B2 | 10/2015 | Figulla et al. | |
| 9,232,992 B2 | 1/2016 | Heidner et al. | |
| 9,259,337 B2 | 2/2016 | Cox et al. | |
| 9,314,326 B2 | 4/2016 | Wallace et al. | |
| 9,526,813 B2 | 12/2016 | Cohn et al. | |
| 9,561,096 B2 | 2/2017 | Kim et al. | |
| 9,579,104 B2 | 2/2017 | Beckham et al. | |
| 9,629,635 B2 | 4/2017 | Hewitt et al. | |
| 9,826,980 B2 | 11/2017 | Figulla et al. | |
| 10,004,510 B2 | 6/2018 | Gerberding | |
| 10,517,604 B2 | 12/2019 | Bowman et al. | |
| 10,653,425 B1 | 5/2020 | Gorochow et al. | |
| 10,743,884 B2 | 8/2020 | Lorenzo | |
| 10,751,066 B2 | 8/2020 | Lorenzo | |
| 11,464,518 B2 | 10/2022 | Connor | |
| 11,672,542 B2 | 1/2023 | Xu et al. | |
| 11,607,226 B2 | 3/2023 | Pedroso et al. | |
| 2001/0044595 A1 | 11/2001 | Reydel et al. | |
| 2002/0068974 A1 | 6/2002 | Kuslich et al. | |
| 2002/0147497 A1 | 10/2002 | Belef et al. | |
| 2002/0169473 A1 | 11/2002 | Sepetka et al. | |
| 2003/0171739 A1 | 9/2003 | Murphy | |
| 2004/0034386 A1 | 2/2004 | Fulton et al. | |
| 2004/0093014 A1 | 5/2004 | Ho et al. | |
| 2004/0153120 A1 | 8/2004 | Seifert et al. | |
| 2004/0210297 A1 | 10/2004 | Lin et al. | |
| 2005/0021072 A1 | 1/2005 | Wallace | |
| 2005/0177103 A1 | 8/2005 | Hunter et al. | |
| 2005/0251200 A1 | 11/2005 | Porter | |
| 2006/0052816 A1 | 3/2006 | Bates et al. | |
| 2006/0064151 A1 | 3/2006 | Gutterman et al. | |
| 2006/0155323 A1 | 7/2006 | Porter et al. | |
| 2007/0088387 A1 | 4/2007 | Eskridge et al. | |
| 2007/0162071 A1 | 7/2007 | Burkett et al. | |
| 2007/0167876 A1 | 7/2007 | Euteneuer et al. | |
| 2007/0191884 A1 | 8/2007 | Eskridge et al. | |
| 2007/0233188 A1 | 10/2007 | Hunt et al. | |
| 2008/0103505 A1 | 5/2008 | Fransen | |
| 2008/0119886 A1 | 5/2008 | Greenhalgh et al. | |
| 2008/0281302 A1 | 11/2008 | Murphy et al. | |
| 2008/0281350 A1 | 11/2008 | Sepetka et al. | |
| 2009/0036877 A1 | 2/2009 | Nardone et al. | |
| 2009/0062841 A1 | 3/2009 | Amplatz et al. | |
| 2009/0227983 A1 | 9/2009 | Griffin et al. | |
| 2009/0287291 A1 | 11/2009 | Becking et al. | |
| 2009/0287294 A1 | 11/2009 | Rosqueta et al. | |
| 2009/0287297 A1 | 11/2009 | Cox | |
| 2010/0023046 A1 | 1/2010 | Heidner et al. | |
| 2010/0211156 A1 | 8/2010 | Linder et al. | |
| 2010/0324649 A1 | 12/2010 | Mattsson et al. | |
| 2011/0112588 A1 | 5/2011 | Linderman et al. | |
| 2011/0137317 A1 | 6/2011 | O'Halloran et al. | |
| 2011/0152993 A1* | 6/2011 | Marchand | A61B 17/12113 623/1.2 |
| 2012/0010644 A1 | 1/2012 | Sideris et al. | |
| 2012/0165732 A1 | 6/2012 | Müller | |
| 2012/0191123 A1 | 7/2012 | Brister et al. | |
| 2012/0283768 A1* | 11/2012 | Cox | A61B 17/1219 606/198 |
| 2012/0323267 A1 | 12/2012 | Ren | |
| 2013/0018414 A1 | 1/2013 | Widomski et al. | |
| 2013/0204351 A1 | 8/2013 | Cox et al. | |
| 2013/0211495 A1 | 8/2013 | Halden et al. | |
| 2013/0261658 A1 | 10/2013 | Lorenzo et al. | |
| 2013/0274863 A1 | 10/2013 | Cox et al. | |
| 2013/0325054 A1 | 12/2013 | Watson | |
| 2014/0005714 A1 | 1/2014 | Quick et al. | |
| 2014/0135812 A1 | 5/2014 | Divino et al. | |
| 2014/0200607 A1 | 7/2014 | Sepetka et al. | |
| 2014/0257361 A1 | 9/2014 | Prom | |
| 2014/0277013 A1 | 9/2014 | Sepetka et al. | |
| 2014/0277096 A1 | 9/2014 | Richter et al. | |
| 2014/0358178 A1 | 12/2014 | Hewitt et al. | |
| 2015/0057703 A1 | 2/2015 | Ryan et al. | |
| 2015/0209050 A1 | 7/2015 | Aboytes et al. | |
| 2015/0272589 A1 | 10/2015 | Lorenzo | |
| 2015/0335333 A1 | 11/2015 | Jones et al. | |
| 2015/0342613 A1 | 12/2015 | Aboytes et al. | |
| 2015/0374483 A1 | 12/2015 | Janardhan et al. | |
| 2016/0022445 A1 | 1/2016 | Ruvalcaba et al. | |
| 2016/0192912 A1 | 7/2016 | Kassab et al. | |
| 2016/0249934 A1 | 9/2016 | Hewitt et al. | |
| 2016/0249935 A1 | 9/2016 | Hewitt et al. | |
| 2017/0027726 A1 | 2/2017 | Oyama | |
| 2017/0079661 A1 | 3/2017 | Bardsley et al. | |
| 2017/0079662 A1 | 3/2017 | Rhee et al. | |
| 2017/0079717 A1 | 3/2017 | Walsh et al. | |
| 2017/0258473 A1 | 9/2017 | Plaza et al. | |
| 2017/0304595 A1 | 10/2017 | Nagasrinivasa et al. | |
| 2017/0312109 A1 | 11/2017 | Le | |
| 2017/0312484 A1 | 11/2017 | Shipley et al. | |
| 2017/0316561 A1 | 11/2017 | Helm et al. | |
| 2017/0319826 A1 | 11/2017 | Bowman et al. | |
| 2017/0333228 A1 | 11/2017 | Orth et al. | |
| 2017/0333236 A1 | 11/2017 | Greenan | |
| 2017/0333678 A1 | 11/2017 | Bowman et al. | |
| 2017/0340333 A1 | 11/2017 | Badruddin et al. | |
| 2017/0340383 A1 | 11/2017 | Bloom et al. | |
| 2017/0348014 A1 | 12/2017 | Wallace et al. | |
| 2017/0348514 A1 | 12/2017 | Guyon et al. | |
| 2018/0206850 A1 | 7/2018 | Wang et al. | |
| 2018/0242979 A1 | 8/2018 | Lorenzo | |
| 2018/0303531 A1 | 10/2018 | Sanders et al. | |
| 2018/0317933 A1 | 11/2018 | Nita et al. | |
| 2018/0338767 A1 | 11/2018 | Dasnurkar et al. | |
| 2019/0110796 A1 | 4/2019 | Jayaraman | |
| 2019/0142567 A1 | 5/2019 | Janardhan et al. | |
| 2019/0192162 A1 | 6/2019 | Lorenzo | |
| 2019/0192165 A1 | 6/2019 | Greene, Jr. et al. | |
| 2019/0192167 A1* | 6/2019 | Lorenzo | A61F 2/90 |
| 2019/0192168 A1* | 6/2019 | Lorenzo | A61B 17/12113 |
| 2019/0223879 A1 | 7/2019 | Jayaraman | |
| 2019/0223881 A1 | 9/2019 | Hewitt et al. | |
| 2019/0328398 A1 | 10/2019 | Lorenzo | |

(56) References Cited

U.S. PATENT DOCUMENTS

| | | | |
|---|---|---|---|
| 2019/0357914 A1 | 11/2019 | Gorochow et al. | |
| 2020/0000477 A1 | 1/2020 | Nita et al. | |
| 2020/0069313 A1 | 3/2020 | Xu et al. | |
| 2020/0268365 A1 | 8/2020 | Hebert et al. | |
| 2020/0367897 A1* | 11/2020 | Wolfe | A61B 17/12113 |
| 2020/0375606 A1 | 12/2020 | Lorenzo | |
| 2021/0007755 A1 | 1/2021 | Lorenzo et al. | |
| 2021/0137526 A1 | 5/2021 | Lee et al. | |
| 2021/0177429 A1 | 6/2021 | Lorenzo | |

FOREIGN PATENT DOCUMENTS

| | | |
|---|---|---|
| CA | 2598048 A1 | 5/2008 |
| CN | 104334117 A | 2/2015 |
| CN | 107374688 A | 11/2017 |
| DE | 102008015781 A1 | 10/2009 |
| DE | 102013106031 A1 | 12/2014 |
| DE | 202008018523 U1 | 4/2015 |
| EP | 1054635 B1 | 11/2000 |
| EP | 1483009 B1 | 12/2004 |
| EP | 1527753 B1 | 5/2005 |
| EP | 1569565 B1 | 9/2005 |
| EP | 1574169 B1 | 9/2005 |
| EP | 1494619 B1 | 1/2006 |
| EP | 1633275 B1 | 3/2006 |
| EP | 1659988 B1 | 5/2006 |
| EP | 1725185 B1 | 11/2006 |
| EP | 1923005 B1 | 5/2008 |
| EP | 2063791 B1 | 6/2009 |
| EP | 2157937 B1 | 3/2010 |
| EP | 2266456 A1 | 12/2010 |
| EP | 2324775 B1 | 5/2011 |
| EP | 2367482 B1 | 9/2011 |
| EP | 2468349 A1 | 6/2012 |
| EP | 2543345 A1 | 1/2013 |
| EP | 2623039 A1 | 8/2013 |
| EP | 2854704 B1 | 4/2015 |
| EP | 2923674 B1 | 9/2015 |
| EP | 3146916 A1 | 3/2017 |
| EP | 3517055 A1 | 7/2019 |
| EP | 3 636 173 A2 | 10/2019 |
| EP | 3 636 171 A1 | 4/2020 |
| JP | 2014-522268 A | 9/2014 |
| JP | 2016-518155 A | 6/2016 |
| WO | WO 03/086240 A1 | 10/2003 |
| WO | WO 2005074814 A2 | 8/2005 |
| WO | WO 2006052322 A2 | 5/2006 |
| WO | WO 2007076480 A2 | 7/2007 |
| WO | WO 2008150346 A1 | 12/2008 |
| WO | WO 2008151204 A1 | 12/2008 |
| WO | WO 2009048700 A1 | 4/2009 |
| WO | WO 2009105365 A1 | 8/2009 |
| WO | WO 2009135166 A2 | 11/2009 |
| WO | WO 2010030991 A1 | 3/2010 |
| WO | WO 2011057002 A2 | 5/2011 |
| WO | WO 2012/034135 A1 | 3/2012 |
| WO | WO 2013025711 A1 | 2/2013 |
| WO | WO 2013159065 A1 | 10/2013 |
| WO | WO 2013162817 A1 | 10/2013 |
| WO | WO 2014078286 A1 | 5/2014 |
| WO | WO 2016107357 A1 | 7/2016 |
| WO | WO 2017/161283 A1 | 9/2017 |
| WO | WO 2019/038293 A1 | 2/2019 |

* cited by examiner

FIG. 3A
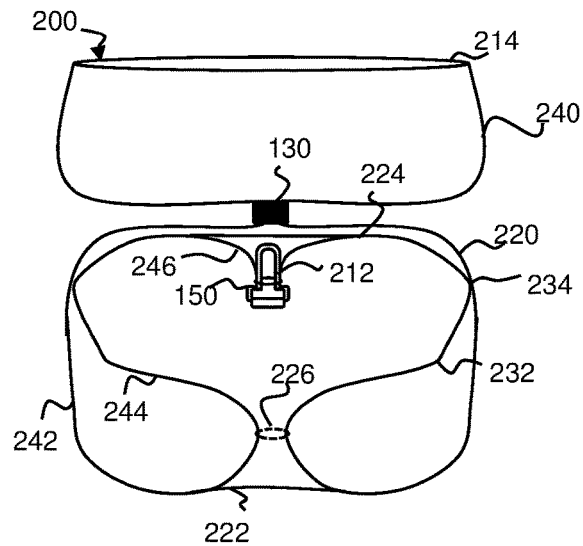
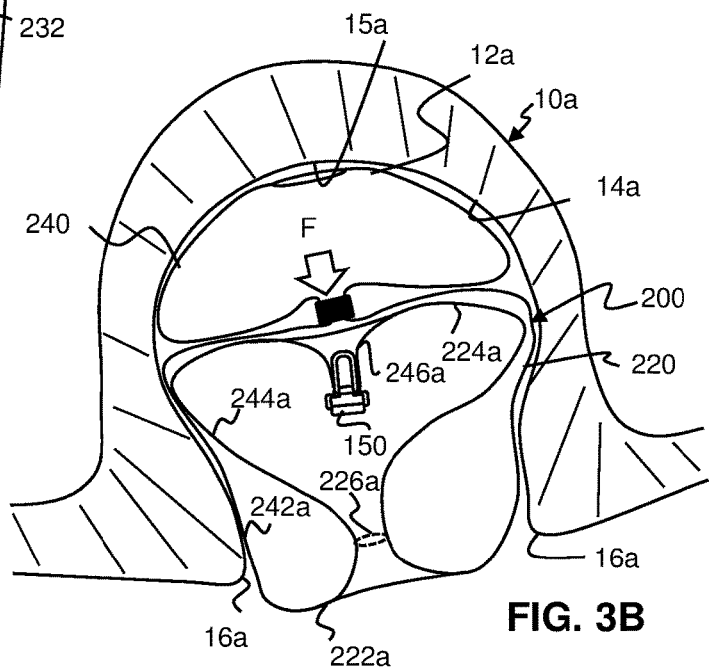
FIG. 3B
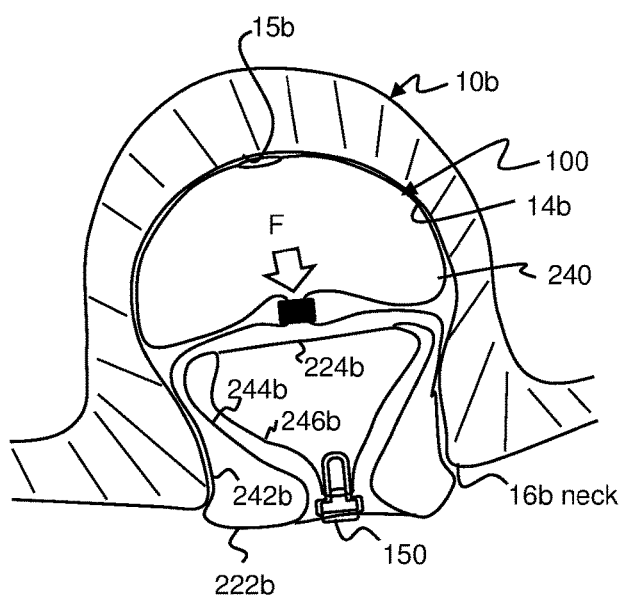
FIG. 3C

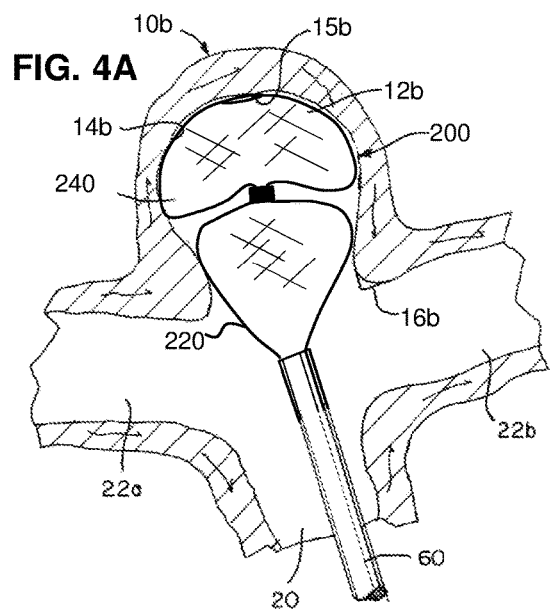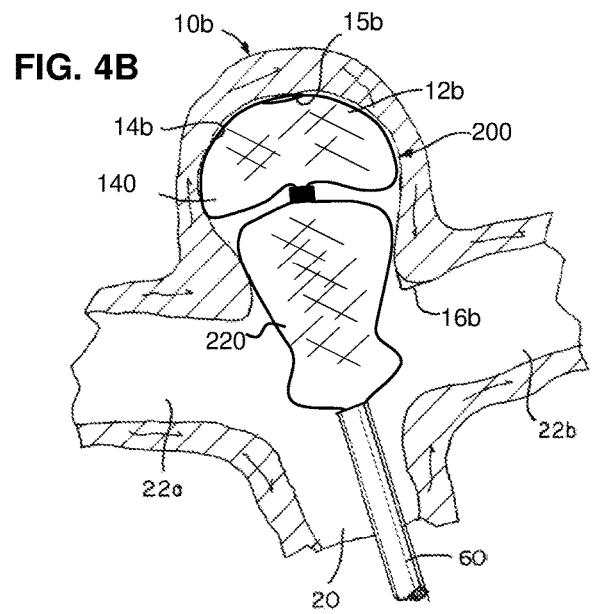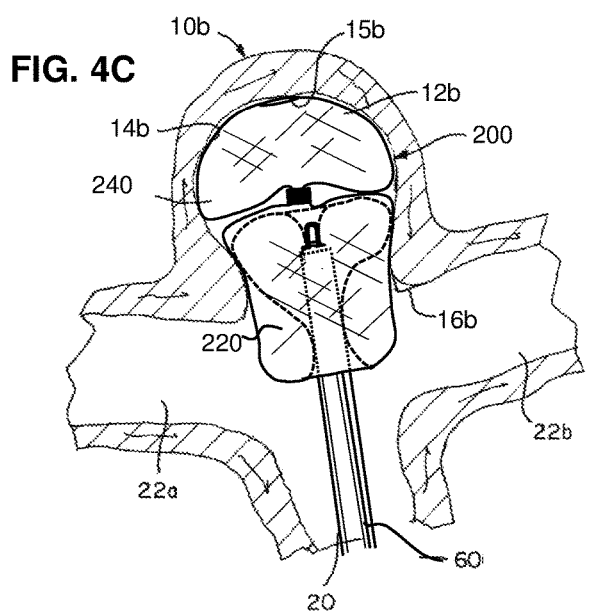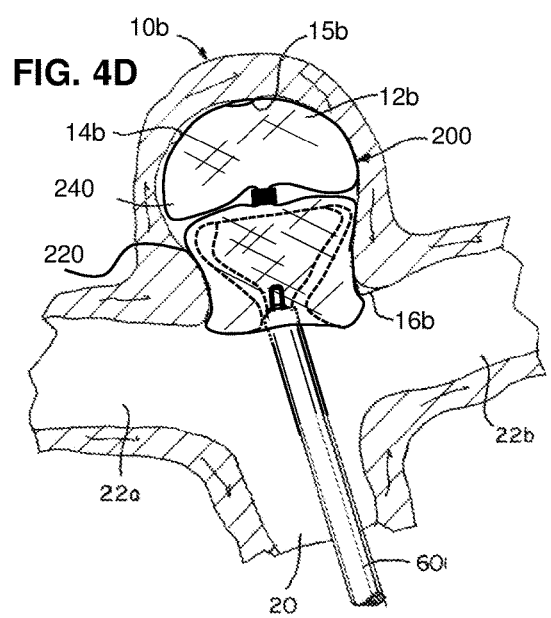

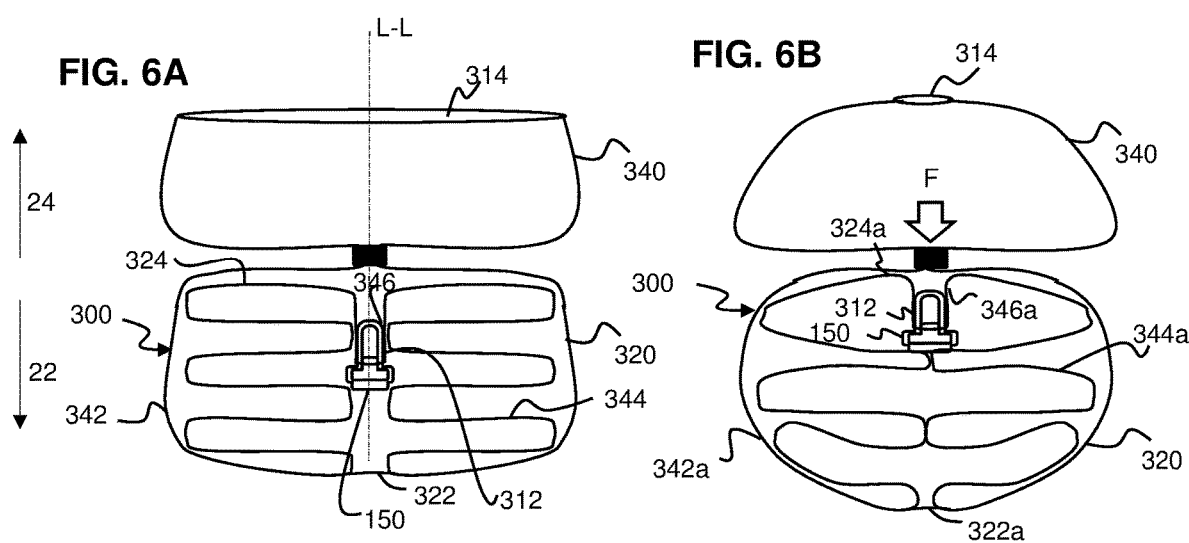
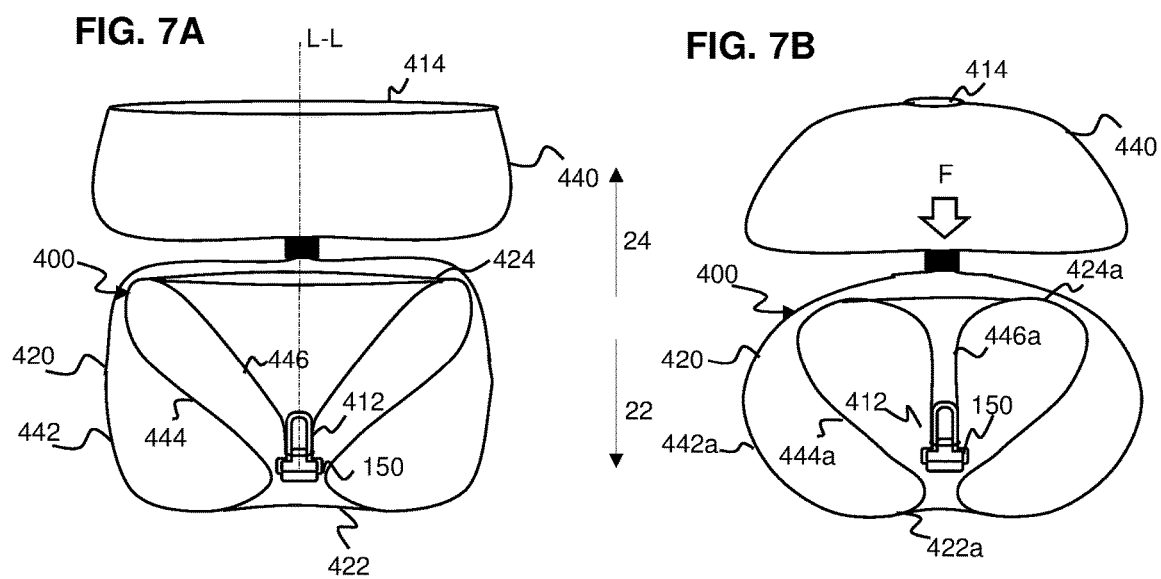

FIG. 10A
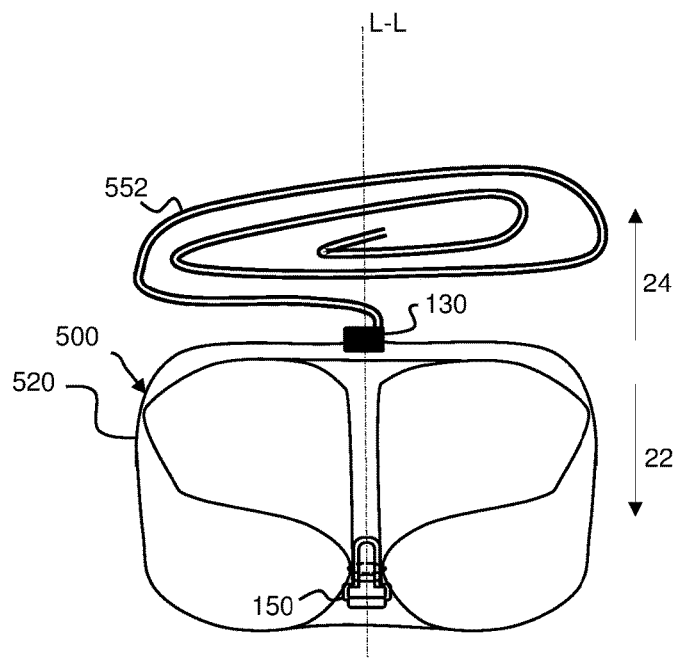
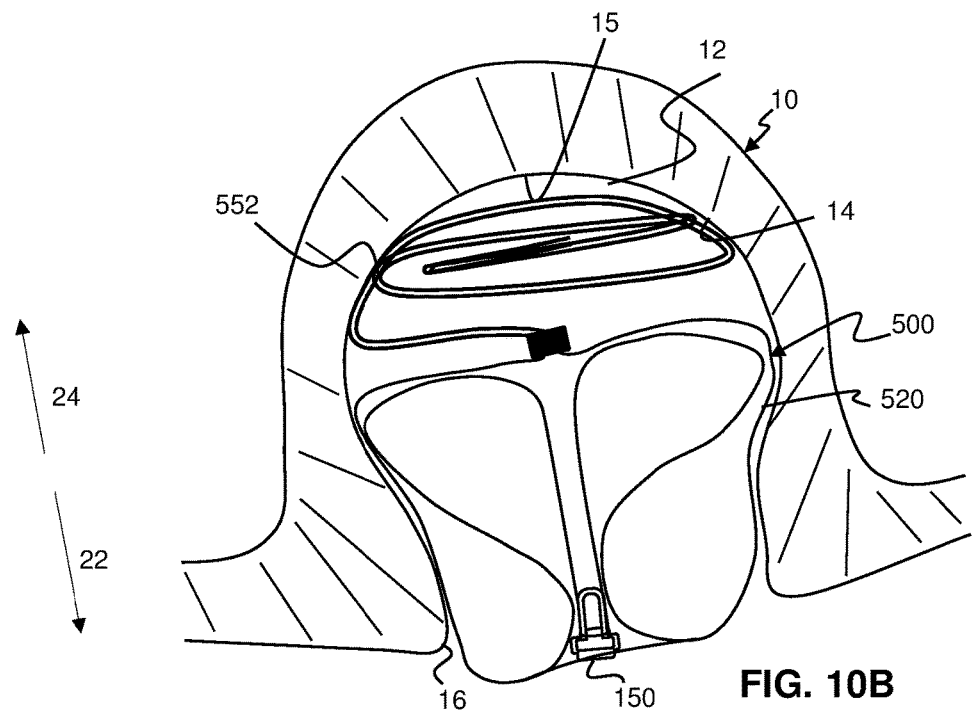
FIG. 10B

FIG. 11A
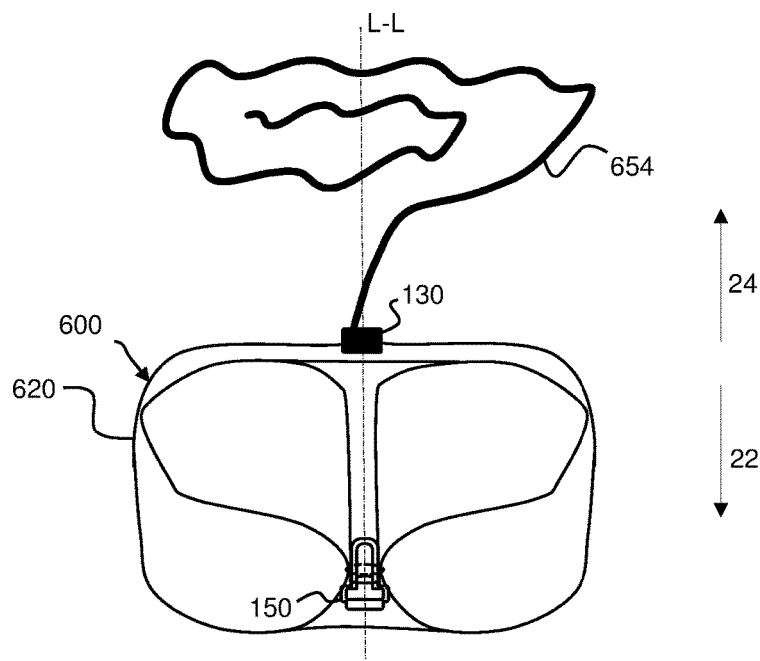
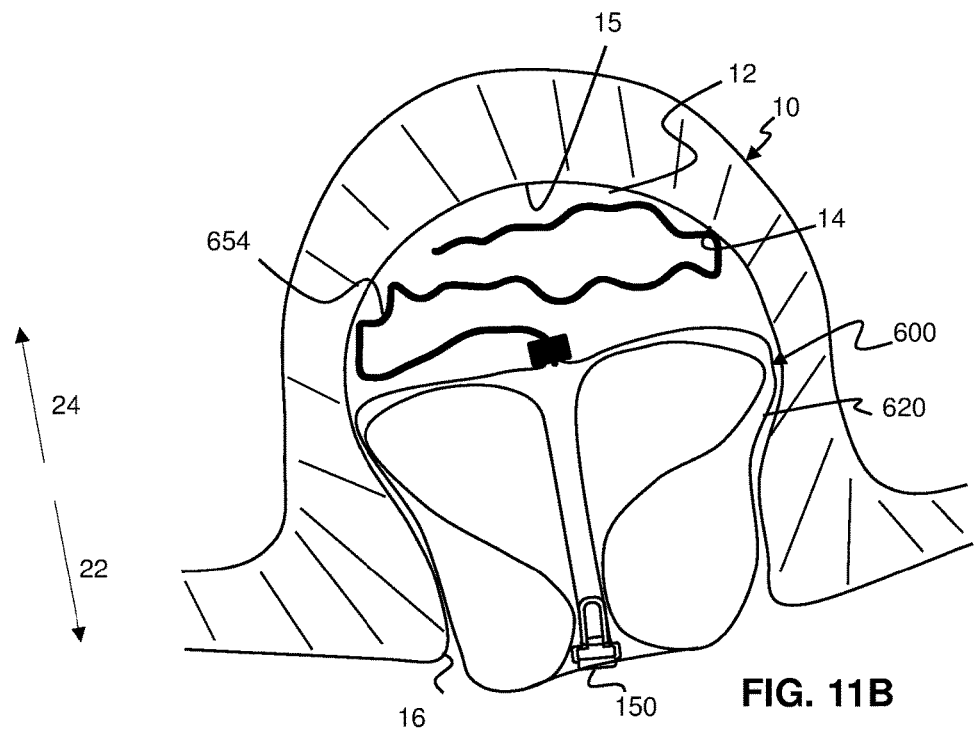
FIG. 11B

INVERTING BRAIDED ANEURYSM IMPLANT WITH DOME FEATURE

CROSS-REFERENCE TO RELATED APPLICATION

The present application claims the benefit of priority under 35 USC § 119 of U.S. Provisional Patent Application No. 63/082,013, filed on Sep. 23, 2020 and incorporated herein by reference in its entirety as if set forth in full into this application.

FIELD

The present invention generally relates to medical instruments, and more particularly, to embolic implants for aneurysm therapy.

BACKGROUND

Cranial aneurysms can be complicated and difficult to treat due to their proximity to critical brain tissues. Current treatments can involve intravascularly delivering embolic coils that fill the sac of the aneurysm or block the entrance or neck of the aneurysm to prevent blood flow into the aneurysm. When filling an aneurysm sac, the embolic coils clots the blood, creating a thrombotic mass within the aneurysm. When treating the aneurysm neck, blood flow into the entrance of the aneurysm is inhibited, inducing venous stasis in the aneurysm and facilitating a natural formation of a thrombotic mass within the aneurysm. Naturally formed thrombotic masses can result in improved healing compared to aneurysm masses packed with embolic material because naturally formed thrombotic masses can reduce the likelihood of distention from arterial walls and facilitate reintegration into the original parent vessel shape along the neck plane. However, properly placing embolic coils across the aneurysm neck can be challenging. Embolic coils delivered to the neck of the aneurysm can potentially have the adverse effect of impeding the flow of blood in the adjoining blood vessel, particularly if the entrance is overpacked. Conversely, if the entrance is insufficiently packed, blood flow can persist into the aneurysm. Whether treating the aneurysm neck or packing the aneurysm with coils, treating certain aneurysm morphology (e.g. wide neck, bifurcation, etc.) can require ancillary devices such a stents or balloons to support the coil mass and obtain the desired packing density. Once implanted, the coils cannot easily be retracted or repositioned. Furthermore, embolic coils do not always effectively treat aneurysms as aneurysms treated with multiple coils often recanalize or compact because of poor coiling, lack of coverage across the aneurysm neck, blood flow, or large aneurysm size.

Tubular braided implants have the potential to easily, accurately, and safely treat an aneurysm or other arteriovenous malformation in a parent vessel without blocking flow into perforator vessels communicating with the parent vessel. A tubular braided implant that can be used in addition to, or as an alternative to embolic coil treatments of aneurysms is disclosed in U.S. Pat. No. 10,653,425, incorporated herein by reference.

SUMMARY

Example implants presented herein can be implanted in an aneurysm to cause thrombogenesis within the aneurysm's sac. Example implants include a braid that can extend across the aneurysm neck and anchor to aneurysm's walls at least in the proximal portion of the aneurysm sac. Example implants can further include a dome feature configured to press into aneurysm walls near the aneurysm's dome at a distal portion of the aneurysm sac. The braid at the aneurysm's neck and the dome feature can be joined or constricted at a junction. The dome feature can facilitate proper anchoring of the braid across the aneurysm's neck. Various examples of implants having variations in dome features and variations in braided portions are presented herein. The dome features and braided portions are interchangeable between examples.

An example implant can include a first braided segment, a second braided segment, and a band. The example implant can be shaped to have a predetermined shape. The first braided segment can include a distal open end. The second braided segment can include a proximal pinched end. The band can be positioned at a junction between the first braided segment and the second braided segment. The band can constrict the first braided segment and the second braided segment at the junction. The first braided segment can function as a dome feature and the second braided segment can be positioned across an aneurysm neck.

In the predetermined shape, the first braided segment can extend in a distal direction from the band and form a bowl shape. In the predetermined shape, the second braided segment can extend in a proximal direction from the band. In the predetermined shape, the second braided segment can include two inversions separating three sections which at least partially overlap each other such that the pinched end is affixed to an innermost section of the three sections, the band is affixed to an outermost section of the three sections, and a middle section of the three sections extends between the two inversions and is positioned within outermost section and around the innermost section.

In the predetermined shape, the entirety of the first braided segment of the implant can be positioned in the distal direction from the entirety of the second braided segment of the implant.

In the predetermined shape, the band and the pinched end can be approximately aligned along a longitudinal axis. The first braided segment and the second braided segment can be respectively approximately radially symmetrical with respect to the longitudinal axis.

The implant can be collapsible to a dimension sized to traverse a microcatheter within neurovasculature.

The implant can be configured to be manipulated at the pinched end to position the implant in an implanted shape in a spherical cavity. The implanted shape can be based in part on the predetermined shape and based in part on the geometry of the spherical cavity.

In the implanted shape, the first braided section can provide a force pressing the second braided section in the proximal direction due to compression of the first braided section against a dome of the spherical cavity.

In the implanted shape, the open end can be positioned approximate a distal wall of the spherical cavity, the band can be suspended within the spherical cavity, and the second braided segment can include two inversions separating three sections which at least partially overlap each other.

The two inversions and the three sections of the second braided segment when the implant is in the implanted shape can correspond approximately to the two inversions and the three sections of the second braided segment when the implant is in the predetermined shape.

In the implanted shape, a diameter of the open end is collapsed in comparison to the diameter of the open end when the implant is in the predetermined shape. In the implanted shape, a height of the first segment is foreshortened in comparison to the height of the first segment when the implant is in the predetermined shape.

The open end can include closed looped braid strands.

The band can include radiopaque material.

The implant can be stable in two different implanted shapes, where the stable shape that the implant takes can be selected during treatment to fit within a smaller or larger spherical cavity. The implant can be stable in a first implanted shape based on the predetermined shape when constrained by a first substantially spherical cavity. The implant can be stable in a second implanted shape based on the predetermined shape when constrained by a second substantially spherical cavity smaller than the first substantially spherical cavity, In the first implanted shape, the open end is positioned approximate a distal wall of the first substantially spherical cavity, the band is suspended within the first substantially spherical cavity, and the second braided segment includes two inversions separating three sections which at least partially overlap each other. The two inversions and the three sections of the second braided segment when the implant is in the first implanted shape correspond approximately to the two inversions and the three sections of the second braided segment when the implant is in the predetermined shape.

In the second implanted shape, the open end is positioned approximate a distal wall of the second substantially spherical cavity, the band is suspended within the second substantially spherical cavity, and the second braided segment includes two inversions separating three sections which at least partially overlap each other. One of the two inversions, when the implant is in the second implanted shape, corresponds to a bend in the middle section when the implant is in the predetermined shape.

An example method for constructing an implant can include one or more of the following steps presented in no particular order, and the method can include additional steps not included here. A band can be affixed between a first braided segment and a second braided segment, the first braided segment including a distal open end and the second braided segment including a proximal pinched end. The implant can be shaped to a predetermined shape to which the implant is capable of self-expanding. Shaping the implant to the predetermined shape can include: forming the first braided segment to a bowl shape extending in a distal direction from the band; inverting the second braided segment to form a proximal inversion folded toward the distal direction thereby defining an outermost section of the second braided segment; and inverting the second braided segment to form a distal inversion folded toward the proximal direction thereby defining a middle section between the proximal and distal inversions of the second braided segment that is at least partially surrounded by the outermost section and defining an innermost section between the distal inversion and the pinched end that is at least partially surrounded by the middle section.

The method can further include shaping the implant to the predetermined shape such that when the implant is in the predetermined shape, the entirety of the first braided segment is positioned in the distal direction from the entirety of the second braided segment.

The method can further include shaping the implant to the predetermined shape such that when the implant is in the predetermined shape, the band and the pinched end are approximately aligned along a longitudinal axis and the first braided segment and the second braided segment are respectively approximately radially symmetrical with respect to the longitudinal axis.

The method can further include collapsing the implant and positioning the implant in a microcatheter sized to traverse neurovasculature.

The method can further include affixing a delivery system to the implant approximate the pinched end so that the pinched end can be manipulated to move the implant from a distal end of the microcatheter.

The method can further include forming a bend in the middle section of the second braided segment that is configured to fold to form an inversion when the implant is positioned, via manipulation of the pinched end, in a substantially spherical cavity.

An example method of treating an aneurysm can include one or more of the following steps presented in no particular order, and the method can include additional steps not included here. An open end of a first braided segment of an implant can be pushed from a distal end of a microcatheter into a sac of an aneurysm. The first braided segment can be shaped to form a distal sack positioned against a dome of the aneurysm and extending centrally through the sac to a band affixed to the first braided segment. An outer section of a second braided segment of the implant can be shaped to form proximal sack extending centrally through the sac from the band, positioned against a portion of the aneurysm wall in a proximal direction from the distal sack, and extending across at least a portion of a neck opening of the aneurysm. The second braided segment can be inverted approximate the neck opening of the aneurysm. The second braided segment can be inverted within the proximal sack.

The method can further include pressing the distal sack into the dome.

The method can further include implanting embolic coils near a distal wall of the aneurysm.

The method can further include pressing the distal sack into the embolic coils.

The method can further include releasing the implant in an implanted configuration such that the first braided segment provides a force to press the second braided segment in the proximal direction.

The implant can have a predetermined shape in which the second braided segment includes two inversions separating three sections which at least partially overlap each other such that the pinched end is affixed to an innermost section of the three sections, the band is affixed to an outermost section of the three sections which forms the proximal sack, a middle section of the three sections extends between the two inversions, the middle section is positioned within outermost section and around the innermost section, and the middle section includes a bend. The step of inverting the second braided segment within the proximal sack can include folding the middle section at the bend such that the bend forms an inversion of the second braided segment within the proximal sack.

Another example implant can include an embolic coil, a braided segment, and a band positioned at a junction between the embolic coil and braided segment. The implant can have a predetermined shape in which the embolic coil extends in a distal direction from the band forming a spiral shape and the braided segment extends in a proximal direction from the band and comprises two inversions separating three sections. The three section can at least partially overlap each other. The braided segment can have a pinched end that is affixed to an innermost section of the three sections. The band can be affixed to an outermost section of the three sections. A middle section of the three sections can extend between the two inversions and can be positioned within the outermost section and around the innermost section. The braided segment can otherwise be configured similarly to the second braided segment or proximal braided segment of any example braided implant described herein.

Another example method for constructing an implant can include one or more of the following steps presented in no particular order, and the method can include additional steps not included here. A band can be affixed at a junction between an embolic coil and a distal end of a braided segment. The implant can be shaped to a predetermined shape to which the implant is capable of self-expanding. The shaping can include forming the embolic coil to a spiral shape extending in a distal direction from the band; inverting the braided segment to form a proximal inversion folded toward the distal direction thereby defining an outermost section of the second braided segment; and inverting the braided segment to form a distal inversion folded toward the proximal direction thereby defining a middle section between the proximal and distal inversion of the second braided segment that is at least partially surrounded by the outermost section and defining an innermost section between the distal inversion and the pinched end that is at least partially surrounded by the middle section. The example method can further include any of the steps for shaping the braided segment as described in any other example method for constructing an implant presented herein as such methods relate to shaping a second braided segment or a proximal braided segment.

Another method of treating an aneurysm can include one or more of the following steps presented in no particular order, and the method can include additional steps not included here. An embolic coil of an implant can be pushed from a distal end of a microcatheter into a sac of an aneurysm. The embolic coil can be positioned against a distal wall of the aneurysm. A band joining the embolic coil to the braided segment can be positioned within the aneurysm sac. The braided segment can be shaped to include two inversions. The braided segment can be released from a delivery system such that the braided segment remains anchored within the aneurysm sac. The example method can further include any of the steps for implanting the braided segment as described in any other example method of treatment presented herein as such methods relate to implanting a second braided segment or a proximal braided segment.

Another example implant can include a wire frame, a braided segment, and a band positioned at a junction between the wire frame and the braided segment. The implant can have a predetermined shape in which the wire frame extends in a distal direction from the band forming a spiral shape and the braided segment extends in a proximal direction from the band and includes two inversions separating three sections which at least partially overlap each other. A pinched end of the braided segment can be is affixed to an innermost section of the three sections. The band can be affixed to an outermost section of the three sections. A middle section of the three sections can extend between the two inversions and can be positioned within the outermost section and around the innermost section. The braided segment can otherwise be configured similarly to the second braided segment or proximal braided segment of any example braided implant described herein.

Another example method for constructing an implant can include one or more of the following steps presented in no particular order, and the method can include additional steps not included here. A band can be affixed at a junction between a wire frame and a distal end of a braided segment. The implant can be shaped to a predetermined shape to which the implant can be capable of self-expanding. The shaping can include forming the wire frame to a spiral shape extending in a distal direction from the band; inverting the braided segment to form a proximal inversion folded toward the distal direction thereby defining an outermost section of the second braided segment; and inverting the braided segment to form a distal inversion folded toward the proximal direction thereby defining a middle section between the proximal and distal inversion of the second braided segment that is at least partially surrounded by the outermost section and defining an innermost section between the distal inversion and a pinched end of the braided segment that is at least partially surrounded by the middle section. The example method can further include any of the steps for shaping the braided segment as described in any other example method for constructing an implant presented herein as such methods relate to shaping a second braided segment or a proximal braided segment.

Another method of treating an aneurysm can include one or more of the following steps presented in no particular order, and the method can include additional steps not included here. A wire frame of an implant can be pushed from a distal end of a microcatheter into a sac of an aneurysm. The wire frame can be positioned against a distal wall of the aneurysm. A band joining the wire frame to a braided segment of the implant can be positioned within the aneurysm sac. The braided segment can be shaped to include two inversions. The braided segment can be released from a delivery system such that the braided segment remains anchored within the aneurysm sac. The example method can further include any of the steps for implanting the braided segment as described in any other example method of treatment presented herein as such methods relate to implanting a second braided segment or a proximal braided segment.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIG. 3A is an illustration of another example implant in a predetermined shape according to aspects of the present invention.

FIGS. 3B and 3C are illustrations of the example implant illustrated in FIG. 3A in two stable implanted shapes according to aspects of the present invention.

FIGS. 4A through 4D are a sequence of illustrations depicting another example aneurysm treatment according to aspects of the present invention.

FIGS. 6A and 6B are illustrations of another example implant in a predetermined shape (FIG. 6A) and an implanted shape (FIG. 6B) according to aspects of the present invention.

FIGS. 7A and 7B are illustrations of another example implant in a predetermined shape (FIG. 7A) and an implanted shape (FIG. 7B) according to aspects of the present invention.

FIGS. 10A and 10B are illustrations of another example implant in a predetermined shape (FIG. 10A) and an implanted shape (FIG. 10B) according to aspects of the present invention.

FIGS. 11A and 11B are illustrations of another example implant in a predetermined shape (FIG. 11A) and an implanted shape (FIG. 11B) according to aspects of the present invention.

DETAILED DESCRIPTION

Figure 1A:
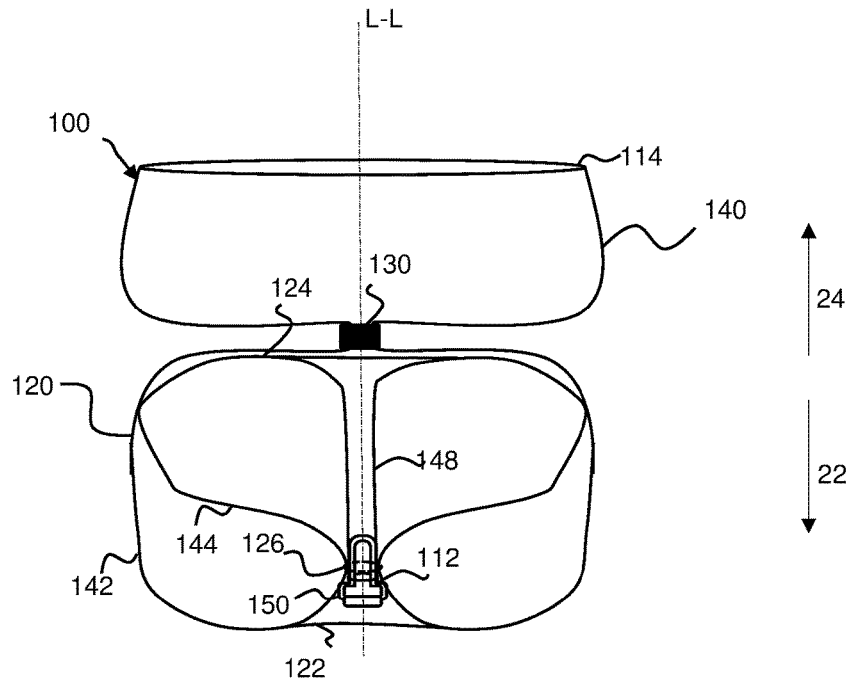
FIG. 1A is an illustration of an example implant in a predetermined shape according to aspects of the present invention.
Figure 1B:
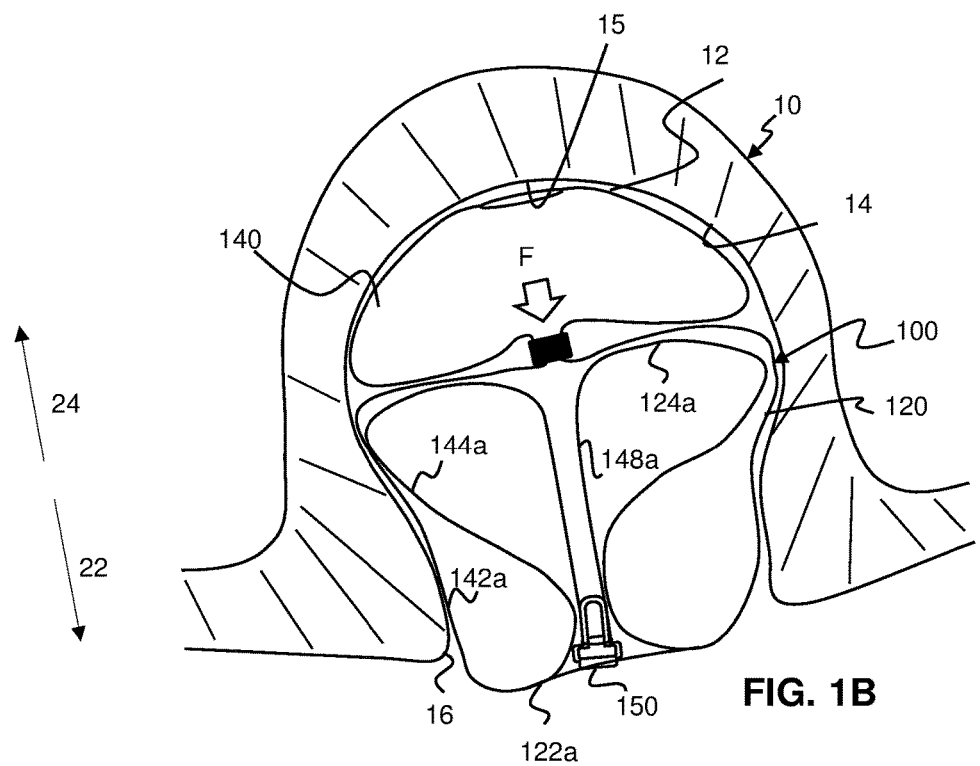
FIG. 1B is an illustration of the example implant illustrated in FIG. 1A in an implanted shape according to aspects of the present invention.

FIGS. 1A and 1B are illustrations of a profile of an example implant 100 that can have a predetermined shape as illustrated in FIG. 1 and an implanted shape as illustrated in FIG. 1B. The implant 100 can include a distal braided segment 140 and a proximal braided segment 120, where a distal direction 24 and a proximal direction 22 are defined in relation to a physician administering the treatment. The braided segments 120, 140 can each be separate braids that are joined by a band 130 or can be a contiguous braid constricted by the band 130. Alternatively, the braided segments 120, 140 can be joined or constructed by an adhesive, suture, or other suitable material or component.

The band 130 preferably includes radiopaque material. The radiopaque material can allow the band 130 to function as fluoroscopic marker that can be visualized during implantation as an indication of the position of the implant 100.

The distal braided segment 140 can have an open end 114. The proximal braided segment 120 can have a pinched end 112 attached to a detachment feature 150. The detachment feature 150 is illustrated as a flat key that can be used with a mechanical implant delivery system (not illustrated).

The braided segments 120, 140 can include memory shape material that can be heat set to the predetermined shape, can be deformed for delivery through a catheter (FIG. 2A), and can self-expand to the implanted shape (FIG. 1B) that is based on the predetermined shape and confined by the anatomy of an aneurysm 10 in which it is implanted.

FIG. 1A illustrates the predetermined shape of the implant 100 in which the distal braided segment 140 extends in a distal direction 24 from the band 130 forming a bowl shape and the proximal braided segment 120 extends in the proximal direction 22 from the band 130 and includes two inversions 122, 124 separating three sections 142, 144, 148 which at least partially overlap each other. The pinched end 112 is affixed to an innermost section 148 of the three sections. The band 130 is affixed to an outermost section 142 of the three sections. A middle section 144 of the three sections extends between the two inversions 122, 124 and is positioned within outermost section 142 and around the innermost section 148.

In the illustrated predetermined shape, the entirety of the distal braided segment is positioned in the distal direction 24 from the entirety of the proximal braided segment 120. In the predetermined shape, the band 130 and the pinched end 112 can be approximately aligned along a longitudinal axis (L-L). The distal braided segment 140 and the proximal braided segment 120 can be respectively approximately radially symmetrical with respect to the longitudinal axis (L-L).

FIG. 1B illustrates the distal braided segment 140 functioning as a dome feature pressing into walls 14 of the aneurysm 10 near a dome 15 or distal portion of the aneurysm walls 14. FIG. 1B illustrates the proximal braided segment 120 extending across a neck 16 of the aneurysm 10 and anchoring to aneurysm's walls 14 at least in a proximal portion of the aneurysm sac 12. Implanted as such, the implant 100 provides sufficient coverage across the aneurysm neck 16 to induce venous stasis in the aneurysm sac 12 and provides a low density of embolic material within the aneurysm sac 12 so that a majority of thrombotic mass within the aneurysm 10 following treatment is naturally formed. The distal braided segment 140 provides a force (F) in the proximal direction 22 to inhibit the proximal braided segment 120 from moving distally into the aneurysm sac 12.

In the implanted shape, the proximal braided segment 120 can have an outer layer 142a contacting the aneurysm's wall 14, a sack 144a nested within the outer layer 142a, a proximal inversion 122a positioned at the aneurysm's neck 16, and a distal inversion 124a positioned near the band 130. An inner layer 148a of the proximal braided segment 120 can form a compaction resistant column extending from approximate the band 130 to approximate the aneurysm's neck 16 through the sack 144a. The proximal braided segment 120 can be constricted radially when implanted so that the outer layer 142a presses into the aneurysm walls 14 as it moves toward the predetermined shape (FIG. 1A) and is inhibited from attaining the predetermined shape due to confinement within the aneurysm 10. Further, the sack 144a can press into the outer layer 142a to facilitate anchoring of the proximal braided segment 120.

The outer layer 142a of the proximal braided segment 120 in the implanted shape can correspond to the outer layer 142 in the predetermined shape, the proximal inversion 122a in the implanted shape can correspond to the inversion 122 adjacent to the outer layer 142 in the predetermined shape, the sack 144a in the implanted shape can correspond to the middle section 144 in the predetermined shape, the distal inversion 124a in the implanted shape can correspond to the inversion 124 adjacent to the innermost section 148 in the predetermined shape, and the inner layer 148a in the implanted shape can correspond to the innermost section 148 in the predetermined shape. In the implanted shape, the sack 144a can have a neck opening 126a corresponding to a neck opening 126 in the predetermined shape. Preferably, the neck opening 126a is constricted around the inner layer 148a to inhibit blood from entering the sack 144a.

Figure 2A:
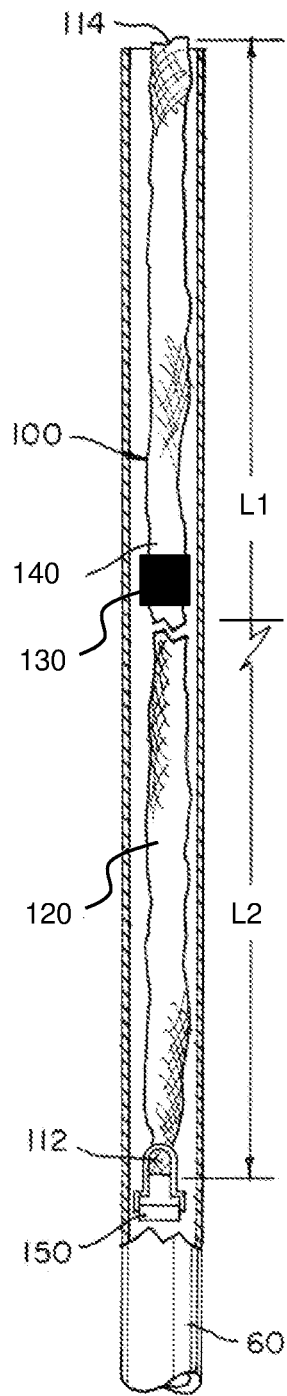
FIGS. 2A through 2G are a sequence of illustrations depicting an example aneurysm treatment according to aspects of the present invention.

FIGS. 2A through 2G are a sequence of illustrations depicting an example aneurysm treatment. FIG. 2A illustrates the implant 100 positioned within a catheter 60. The implant 100 is collapsed for delivery through vasculature.

The braided segments 120, 140 can be tubular. When used herein, the terms "tubular" and "tube" are to be construed broadly and are not limited to a structure that is a right cylinder or strictly circumferential in cross-section or of a uniform cross-section throughout its length. For example, a tubular structure can have a tapered or curved outer surface without departing from the scope of the present invention. As illustrated, each of the braided segments 120, 140 are extended in respective tubular shapes respectively having a single layer of braid. The distal braided segment 140 preferably has a length L1 that is less than the length L2 of the proximal braided segment 120 when each are respectively collapsed to single layer tubular shapes having approximately equal diameter as illustrated in FIG. 2A. A delivery system can be attached to the detachment feature 150 to move the implant 100 through the catheter 60. The implant 100 can be manipulated at the pinched end and the catheter 60 can be manipulated to move the implant 100 through the sequence of treatment steps illustrated in FIGS. 2B through 2G.

Figure 2B:
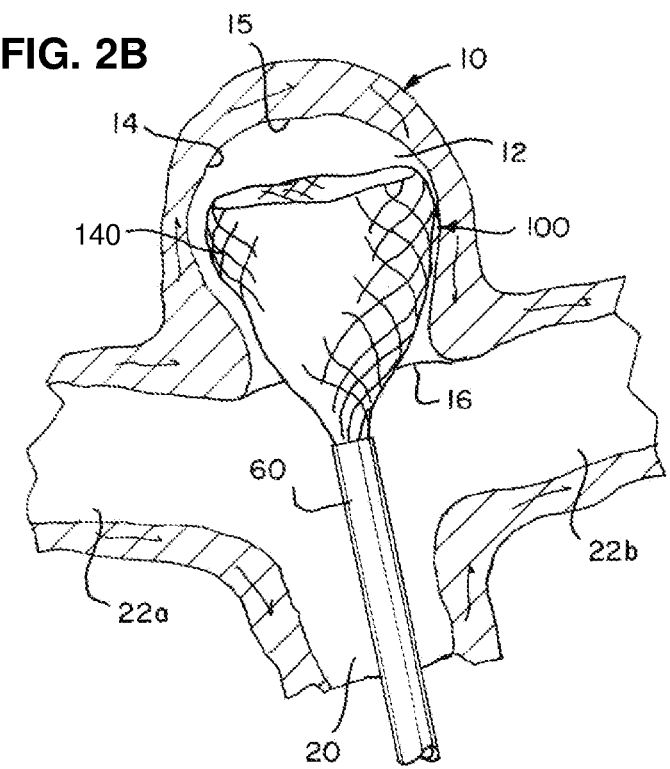

FIG. 2B illustrates the distal braided segment 140 being pushed from the catheter 60 into the sac 12 of the aneurysm 10. The distal braided segment 140 expands toward the bowl shape of the predetermined shape illustrated in FIGS. 1A and 1s inhibited from moving completely to the bowl shape by contacting walls 14 of the aneurysm 10.

Figure 2C:
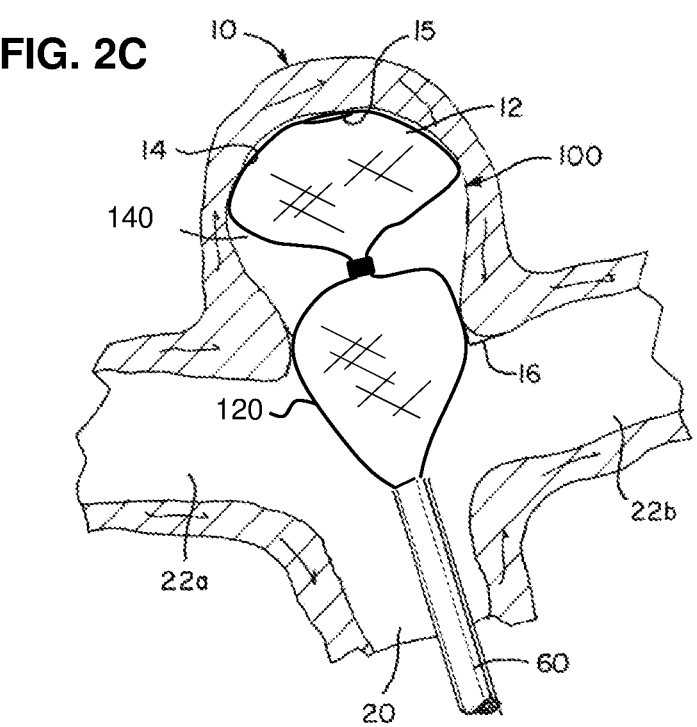

FIG. 2C illustrates the distal braided segment 140 pressed into the dome 15 of the aneurysm wall 14, the band 130 being positioned in the aneurysm sac 12, and the proximal braided segment 120 beginning to be expelled from the catheter 60. When the band 130 includes radiopaque material, the band 130 can be visualized within the aneurysm sac 12 to confirm that the distal braided segment 140 is completely expelled from the catheter 60. A portion of the proximal braided segment 120 corresponding to the outer layer 142 in the predetermined shape is illustrated as expanding outwardly to move toward the predetermined shape of the outer layer 142. The expelled portion of the proximal braided segment 120 is inhibited from moving completely to the predetermined shape as it comes into contact with aneurysm walls 14 and neck opening 16.

Figure 2D:
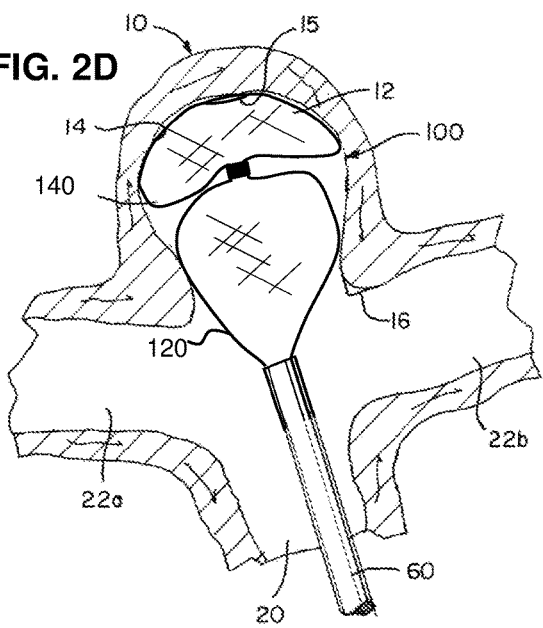

FIG. 2D illustrates the distal braided segment 140 pressed further into the dome 15 and additional braid from the proximal braided segment 120 being expelled from the catheter 60.

Figure 2E:
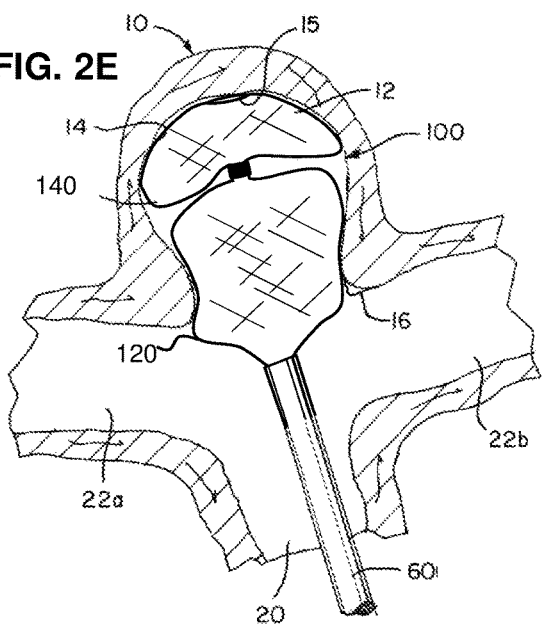

FIG. 2E illustrates the proximal braided segment 120 expanding to conform to the aneurysm walls 14 and neck opening 16 as the proximal braided segment 120 is further expelled from the catheter 60.

Figure 2F:
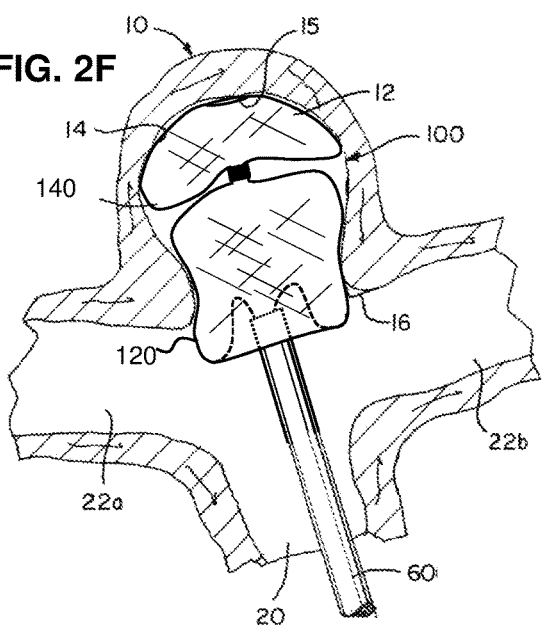

FIG. 2F illustrates the proximal braided segment 120 beginning to invert near the neck opening 16 as the proximal braided segment 120 is further expelled from the catheter 60.

Figure 2G:
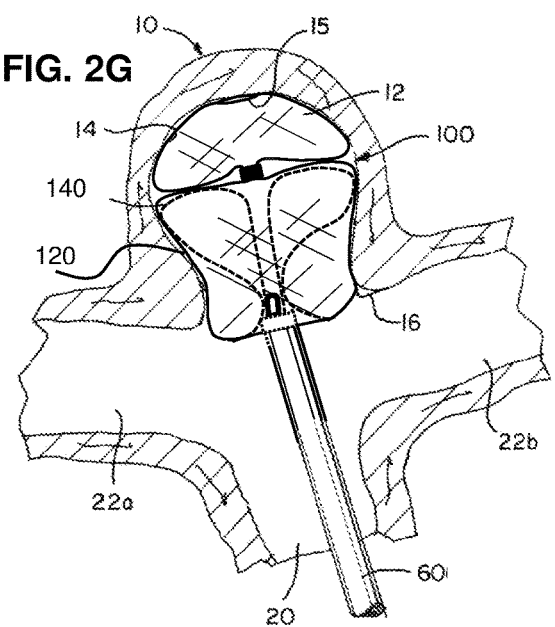

FIG. 2G illustrates the proximal braided segment 120 fully expelled so that the implant 100 is in an implanted shape similar to as illustrated in FIG. 1B. The detachment feature 150 can be disengaged and the catheter 60 can be retracted to leave the implant 100 implanted as illustrated in FIG. 1B.

FIG. 3A is an illustration of another example implant 200 in a predetermined shape. FIGS. 3B and 3C are illustrations of the example implant 200 in two stable implanted shapes. The implant 200 can treat a range of aneurysm sizes including a larger aneurysm 10*a* as illustrated in FIG. 3B and a smaller aneurysm 10*b* as illustrated in FIG. 3C. The implant 200 can have a first implanted shape (FIG. 3B) that can be conducive for treating larger aneurysms 10*a* and a second implanted shape (FIG. 3C) that can be conducive for treating smaller aneurysms 10*b*. The implant 200 can include a distal braided segment 240 having an open end 214 and a predetermined shape similar to that of the distal braided segment 140 of the implant 100 illustrated in FIG. 1A. The implant 200 can include a proximal braided segment 220 having a pinched end 212 and two inversions 222, 224 similar to corresponding features 112, 122, 124 of the proximal braided segment 120 of the implant 100 illustrated in FIG. 1A. The proximal braided segment 220 can have an outermost section 242 affixed to the band 130, a middle section 244 extending between the two inversions 222, 224, and an innermost section 246 surrounded by the middle section 244 and affixed to the detachment feature 150 at the pinched end 212. Compared to the middle section 144 of the implant 100 illustrated in FIG. 1A, the middle section 244 of the implant 200 illustrated in FIG. 3A can further include one or more bends 232, 234 to facilitate movement of the implant 200 into the implanted shape illustrated in FIG. 3C. Compared to the innermost section 148 of the implant 100 illustrated in FIG. 1A, the innermost section 246 of the implant 200 illustrated in FIG. 3A can be truncated so that the pinched end 112 (and thereby the detachment feature 150) is suspended within a sack formed by the middle section 244 when the implant 200 is in the predetermined shape.

FIG. 3B illustrates the implant 200 in a first implanted shape in the larger aneurysm 10*a* having a substantially spherical cavity that is larger than a substantially spherical cavity of the smaller aneurysm 10*b* illustrated in FIG. 3C. In the first implanted shape illustrated in FIG. 3B, the open end 214 is positioned approximate a distal wall, dome 15*a* of the larger aneurysm 10*a*, the band 130 is suspended within a sac 12*a* of the larger aneurysm 10*a*, and the proximal braided segment 220 has two inversions 222*a*, 224*a* separating three sections 242*a*, 244*a*, 246*a* which at least partially overlap each other. The two inversions 222*a*, 224*a* and the three sections 242*a*, 244*a*, 246*a* of the proximal braided segment 220 when the implant is in the first implanted shape correspond approximately to the two inversions 222, 224 and the three sections 242, 244, 246 of the proximal braided segment 220 when the implant 200 is in the predetermined shape as illustrated in FIG. 3A. The proximal braided segment 220 is anchored into the aneurysm walls 14*a* at least in part by a force F in the proximal direction 22 from the distal braided segment 240 so that the proximal braided segment 220 remains in place across the aneurysm neck 16*a*. In the implanted shape, the sack 244*a* can have a neck opening 226*a* corresponding to a neck opening 226 in the predetermined shape.

The first implanted shape of the implant 200 illustrated in FIG. 3B can be similar to that of the implanted shape of the implant 100 illustrated in FIG. 1B with an exception that the inner layer 246*a* of the implant 200 illustrated in FIG. 3B is foreshortened compared to the inner layer 148*a* of the implant 100 illustrated in FIG. 1B. As such, the implant 200 can be implanted in the larger aneurysm 10*a* as illustrated in FIG. 3B following steps similar to those illustrated in FIGS. 2A through 2G.

FIG. 3C illustrates the implant 200 in a second implanted shape in the smaller spherical cavity of the smaller aneurysm 10*b*. In the second implanted shape, the open end 214 is positioned approximate a distal wall, dome 15*b* of the smaller aneurysm 10*b*, the band 130 is suspended within the smaller aneurysm 10*b*, and the second braided segment 220 has two inversions 222*b*, 224*b* separating three sections 242*b*, 244*b*, 246*b* which at least partially overlap each other. One of the two inversions 224*b*, when the implant is in the second implanted shape, corresponds to a bend 232 in the middle section 244 when the implant 200 is in the predetermined shape illustrated in FIG. 3A. The proximal braided segment 220 is anchored into the aneurysm walls 14b at least in part by a force F in the proximal direction 22 from the distal braided segment 240 so that the proximal braided segment 220 remains in place across the aneurysm neck 16b. The proximal braided segment 220 can be radially constricted so that an outer layer 242b presses into the aneurysm wall 14. A middle layer 244b can press into the outer layer 242b to further anchor the proximal braided segment 220. An inner layer 246b can press into the middle layer 244b to further anchor the proximal braided segment 220.

FIGS. 4A through 4D are a sequence of illustrations depicting an example aneurysm treatment where the implant 100 is implanted in the second implanted shape illustrated in FIG. 3C. The treatment sequence can begin following steps similar to as illustrated in FIGS. 2A through 2C. Although not drawn to scale, it should be noted that if implants 100, 200 illustrated in FIGS. 1A and 3A have similar dimensions, the second implanted shape of the implant 200 illustrated in FIG. 3C allows that implant 200 to be implanted in a smaller aneurysm 10b compared to the aneurysm 10 illustrated in FIGS. 2B through 2G. The distal braided segment 240 of the implant 200 illustrated in FIGS. 4A through 4D therefore may occupy a greater percentage of the volume of the smaller aneurysm sac 12b compared to the treatment illustrated in FIGS. 2A through 2G.

FIG. 4A illustrates the distal braided segment 240 pressed into the dome 15b and braid from the proximal braided segment 220 being expelled from the catheter 60.

FIG. 4B illustrates the proximal braided segment 220 expanding to conform to the aneurysm walls 14b and neck opening 16b as the proximal braided segment 220 is further expelled from the catheter 60.

FIG. 4C illustrates the proximal braided segment 220 inverted to a shape similar to that of the first implanted shape illustrated in FIG. 3B. In this shape, the proximal braided segment 220 extends into the vasculature, impeding flow from a stem blood vessel 20 to branch blood vessels 22a, 22b. While it may be possible to leave the proximal braided segment 220 stabilized in this shape when implanted, it may not be desirable to do so.

FIG. 4D illustrates the proximal braided segment 220 collapsed to the second implanted shape similar to that illustrated in FIG. 3C. Movement of the proximal braided segment 220 into the second implanted shape can be accomplished via manipulation of the catheter 60 and the pinched end 212. Bends 232, 234 in the middle section 244 of the proximal braided section 220 in the predetermined shape (FIG. 3A) can promote movement of the proximal braided section 220 from the shape illustrated in FIG. 4C to the second implanted shape illustrated in FIG. 4D. The detachment feature 150 can be disengaged and the catheter 60 can be retracted to leave the implant 200 implanted as illustrated in FIG. 3C.

Figure 5A:
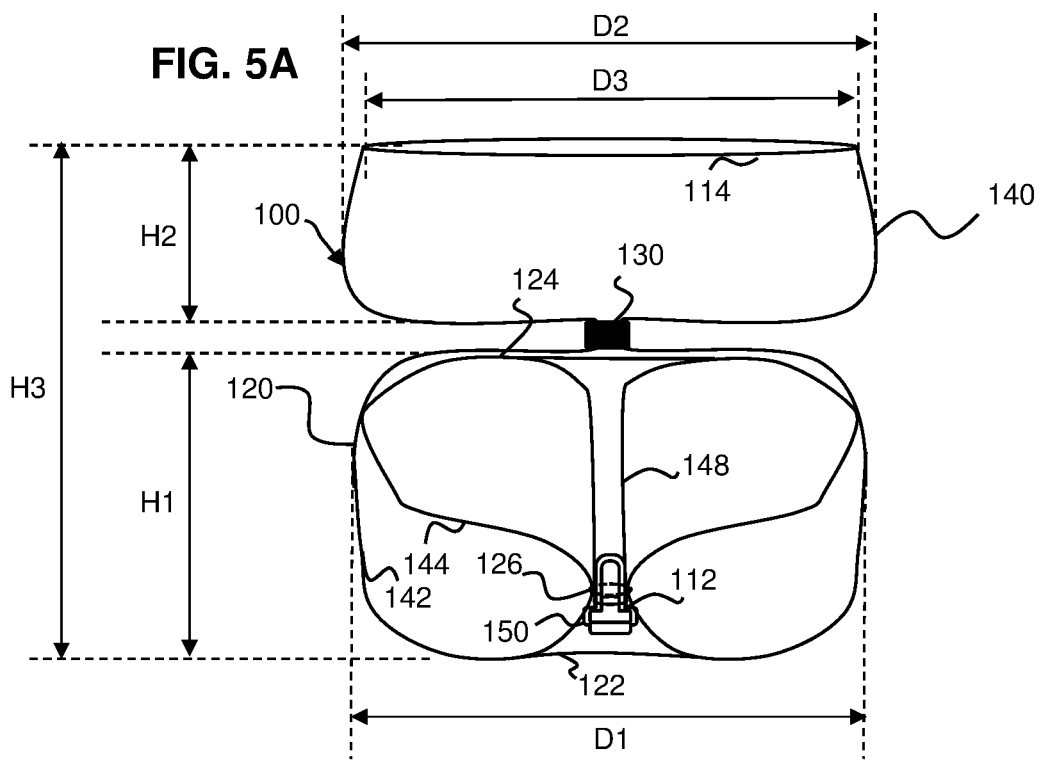
FIG. 5A is an illustration of dimensions of an example implant in a predetermined shape according to aspects of the present invention.

FIG. 5A is an illustration of dimensions of an example implant in a predetermined shape. The proximal braided segment 120 has a height (H1) and a diameter (D1). The distal braided segment 140 has a height (H2) and a diameter (D2). The open end 114 of the distal braided segment 140 has a diameter (D3) about equal to that of the diameter (D2) of the distal braided segment 140. The implant 100 has a height H3 that is at least the sum of the height (H1) of the proximal braided segment 120 and the height (H2) of the distal braided segment 140. Predetermined shapes of other example implants illustrated and described herein, and variations thereof can have similar dimensions.

Figure 5B:
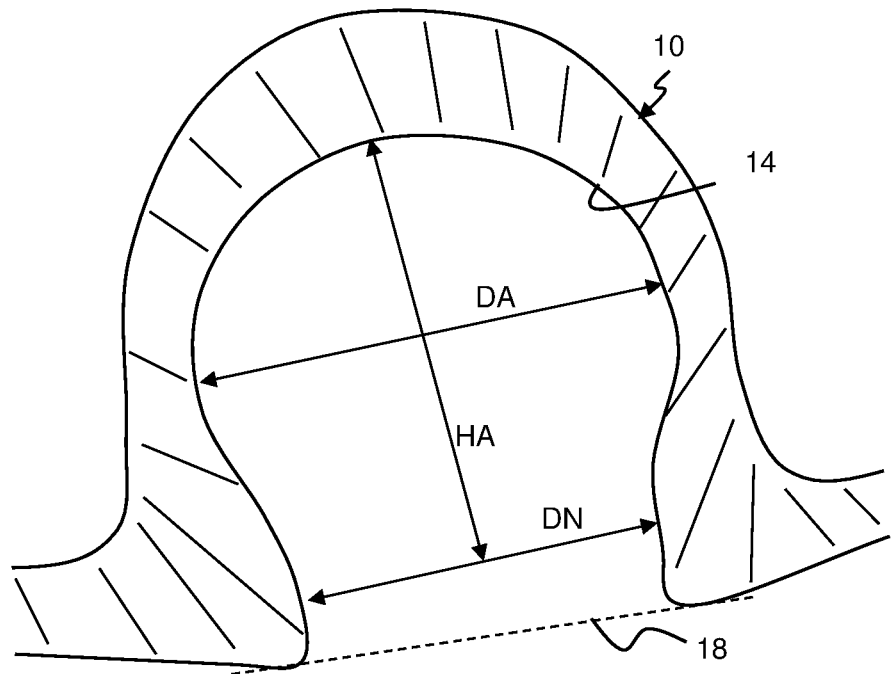
FIG. 5B is an illustration of dimensions of an example aneurysm having a substantially spherical cavity.

FIG. 5B is an illustration of height (HA), sac diameter (DA), and neck diameter (DN) measurements of an aneurysm 10. The location of the plane 18 defining a boundary between the aneurysm 10 and blood vessels is also illustrated. Generally, it is desirable for the diameter (D1) of the proximal braided segment 120 and the diameter (D2) of the distal braided segment 140 to be about equal to, or slightly greater than the sac diameter (DA) so that the distal braided segment 140 and proximal braided segment 120 press radially into the aneurysm walls 14.

Figure 5C:
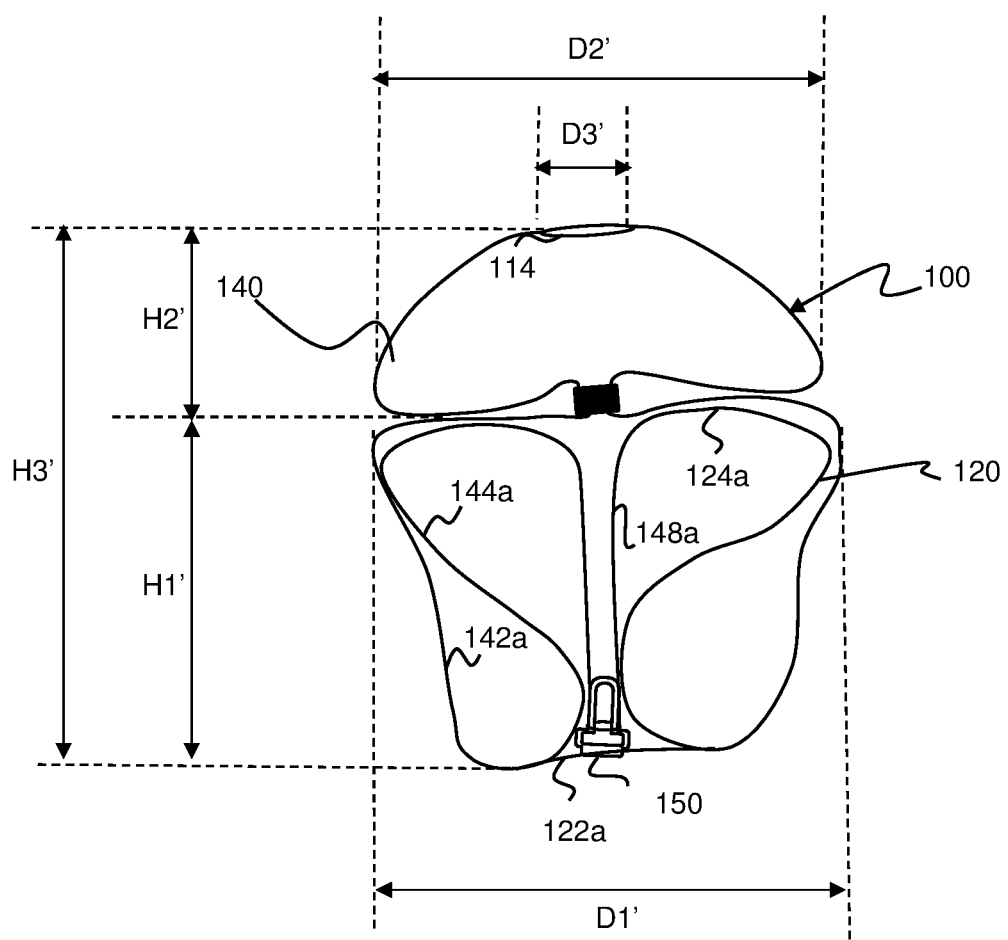
FIG. 5C is an illustration of dimensions of an example implant in an implanted shape according to aspects of the present invention.

FIG. 5C is an illustration of dimensions of an example implant in an implanted shape. The proximal braided segment 120 has a height (H1') and a diameter (D1'). The diameter (D1') of the proximal braided segment 120 in the implanted shape can be collapsed compared to the diameter (D1) of the proximal braided segment 120 in the predetermined shape. The distal braided segment 140 has a height (H2') and a diameter (D2'). A diameter (D3') of the open end 114 of the distal braided segment 140 in the implanted shape can be collapsed relative to the diameter (D3) of the open end 114 distal braided segment 140 in the predetermined shape. In the implanted shape, the implant 100 has a height (H3') that is at least the sum of the height (H1') of the proximal braided segment 120 and the height (H2') of the distal braided segment 140. The height (H3') of the implant 100 can be elongated or collapsed compared to the height (H3) of the implant when in the predetermined shape. Radial constriction of the diameter (D1') of the proximal section 120 can cause elongation of height (H1') of the proximal section, while collapse of the diameter (D3') of the open end 114 and longitudinal compression of the distal braided section 140 can cause foreshortening of the height (H2') of the distal braided section 140 and reduction or elimination of any gap between the distal and proximal braided sections 120, 140. Implanted shapes of other example implants illustrated and described herein, and variations thereof can have similar dimensions.

FIG. 6A is an illustration of an example implant 300 in another alternative predetermined shape. FIG. 6B is an illustration of the example implant 300 in an implanted shape. The implant 300 includes a distal braided segment 340 and a proximal braided segment 320. The distal braided segment 340 can have an open end 314 and be shaped and implanted similarly to the distal braided segments 140, 240 in previous figures. The proximal braided segment 320 can have a pinched end 312 with a detachment feature 150 attached thereto. The implant 300 can be formed in the predetermined shape, collapsed for delivery through a microcatheter, attached to a delivery system at the detachment feature 150, and implanted in the implanted shape.

FIG. 6A illustrates proximal braided segment 320 having two inversions 322, 324, dividing the proximal braided segment 320 into three segments 342, 344, 346 in the predetermined shape. The proximal braided segment 320 can have an outermost section 342 extending from the band 130 to one of the inversions 322, an innermost section 346 extending from the pinched end 312 to the other of the inversions 324, and a middle section 344 extending between the two inversions 322, 324. When in the predetermined shape, the proximal braided segment 320 and distal braided segment 340 can each be substantially radially symmetrical about a central vertical axis.

Comparing the predetermined shape of the proximal braided segment 320 illustrated in FIG. 6A to that of the previously illustrated implants 100, 200, the outermost sections 142, 242, 342 are respectively similar to each other; the innermost section 346 of the implant 300 illustrated in FIG.

6A can be elongated, foreshortened, or any length between the innermost sections 148, 246 of the previously illustrated implants 100, 200; and the middle section 344 of the proximal braided segment 320 illustrated in FIG. 6A has an undulating pattern rather than the "S" shape of the middle section 144, 244 of previously illustrated implants 100, 200. The undulating middle section 344 can be radially symmetrical to form a honeycomb shape. When implanted, the middle section 344 in the undulating pattern can provide a force pattern pressing outwardly to anchor the implant 300 within an aneurysm that is different from a force pattern that could be provided by the middle sections 144, 244 having the "S" shape. The pinched end 312 of the braid 310 in FIG. 6A can be positioned near the inversion 324 adjacent the inner segment 346 as illustrated. Alternatively, the inner segment 346 can be shaped to extend to the inversion 322 adjacent the outer section 342 to provide a compaction resistant column.

FIG. 6B illustrates the proximal braided segment 320 having an outer layer 342a shaped to contact an aneurysm wall, compressed extensions of an undulating middle layer 344a nested within the outer layer 342a, a proximal inversion 322a positioned to be placed an aneurysm neck, and a distal inversion 324a positioned to be placed near the band 130. The detachment feature 150 and pinched end 312 of the proximal braided segment 320 can be positioned within the aneurysm sac, extending from an innermost layer 346a of proximal braided segment 320, either near the distal inversion 324a as illustrated, near the proximal inversion 322a, or at a position in between. The detachment feature 150 and pinched end 312 can be positioned to reduce the likelihood that the implant 300 becomes impacted. The distal braided segment 340 can provide a force F in the proximal direction 22 against the proximal braided segment 320 to anchor the implant 300 within an aneurysm or spherical cavity. The outer layer 342a and middle layer 344a can provide a radially outward force to anchor the implant 30 within an aneurysm or spherical cavity.

FIG. 7A is an illustration of an example implant 400 in another alternative predetermined shape. FIG. 7B is an illustration of the example implant 400 in an implanted shape. The implant 400 has a distal braided segment 440 having an open end 414 and a proximal braided segment 420 having a pinched end 412. A detachment feature 150 can be attached to the proximal braided segment 420 at the pinched end 412. The implant 400 can be formed in the predetermined shape, collapsed for delivery through a microcatheter, attached to a delivery system at the detachment feature 150, and implanted in the implanted shape.

FIG. 7A illustrates the proximal braided segment 420 having two inversions 422, 424, dividing the proximal braided segment 420 into three sections 442, 444, 446. In the predetermined shape, the proximal braided segment 420 can have an outermost section 442 extending from the band 130 to one of the inversions 422, an innermost section 446 extending from the pinched end 412 to the other of the inversions 424, and a middle section 444 extending between the two inversions 422, 424. When in the predetermined shape, the proximal braided segment 420 can be substantially radially symmetrical about a central vertical axis (L-L). The distal braided segment 440 can be shaped and implanted similar to the distal braided segment 140, 240, 340 of previously illustrated implants 100, 200, 300.

Comparing the predetermined shape of the proximal braided segment 420 illustrated in FIG. 7A to that of the implants 100, 200 illustrated in FIGS. 1A and 3A, the outermost sections 142, 242, 442 can be similar to each other, the middle section 444 of the proximal braided segment 420 illustrated in FIG. 7A can have a less pronounced "S" shape compared to the "S" shaped middle section 144, 244 illustrated in FIGS. 1A and 3A, and the innermost section 446 can be conical or "V" shaped in profile with the pinched end 412 positioned near the proximal inversion 422. When implanted, the innermost section 446 can reshape to form a compaction resistant column.

FIG. 7B illustrates the proximal braided segment 420 in an implanted shape having an outer layer 442a shaped to contact an aneurysm wall, a tulip or heart shaped sack 444a nested within the outer layer 442a, a proximal inversion 422a positioned to be placed at an aneurysm neck, a distal inversion 424a positioned to be placed near the band 130, and a compaction resistant column 446a extending within the sack 444a. The detachment feature 150 and pinched end 412 can be positioned within the sack 444a near the proximal inversion 422a. The detachment feature 150 and pinched end 412 can be positioned to reduce the likelihood that the implant 400 becomes impacted. The distal braided segment 440 can provide a force F in the proximal direction 22 against the proximal braided segment 420 to anchor the implant 400 within an aneurysm or spherical cavity. The outer layer 442a and middle layer 444a can provide a radial force to anchor the implant 400 within an aneurysm or spherical cavity.

Figure 8:
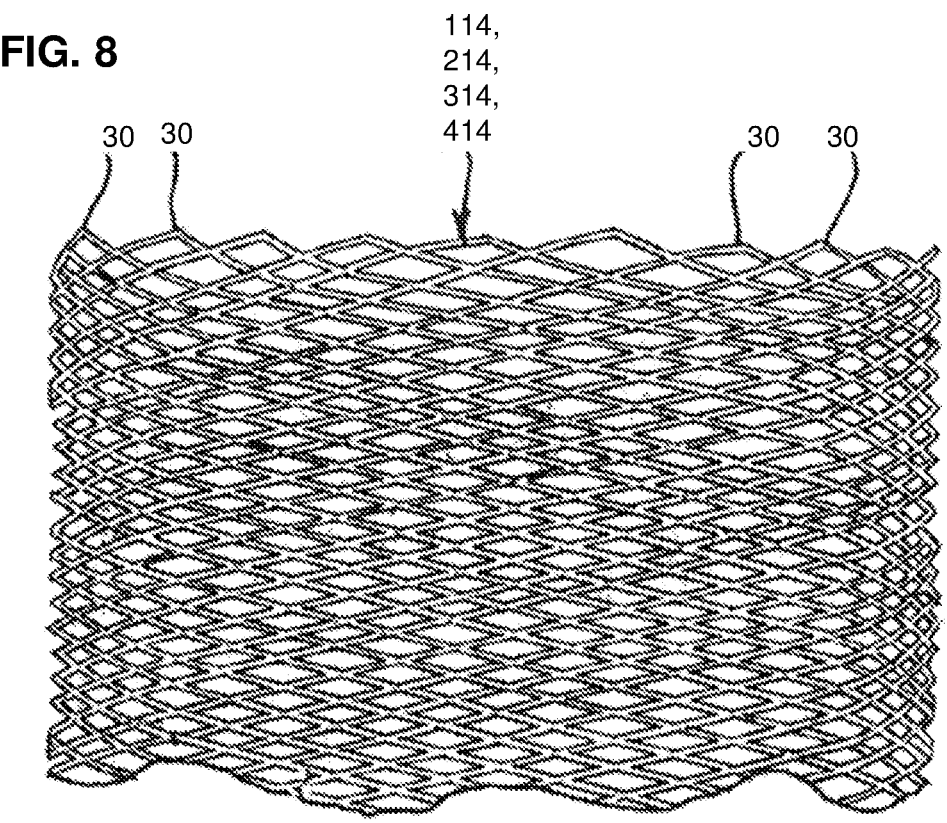
FIG. 8 is an illustration of a braid having closed looped ends according to aspects of the present invention.

FIG. 8 is an illustration of a braid having closed looped ends 30. The braid can be positioned so that the closed looped ends 30 correspond to the open end 114, 214, 314, 414 of any of the previously illustrated implants 100, 200, 300, 400.

Figure 9:
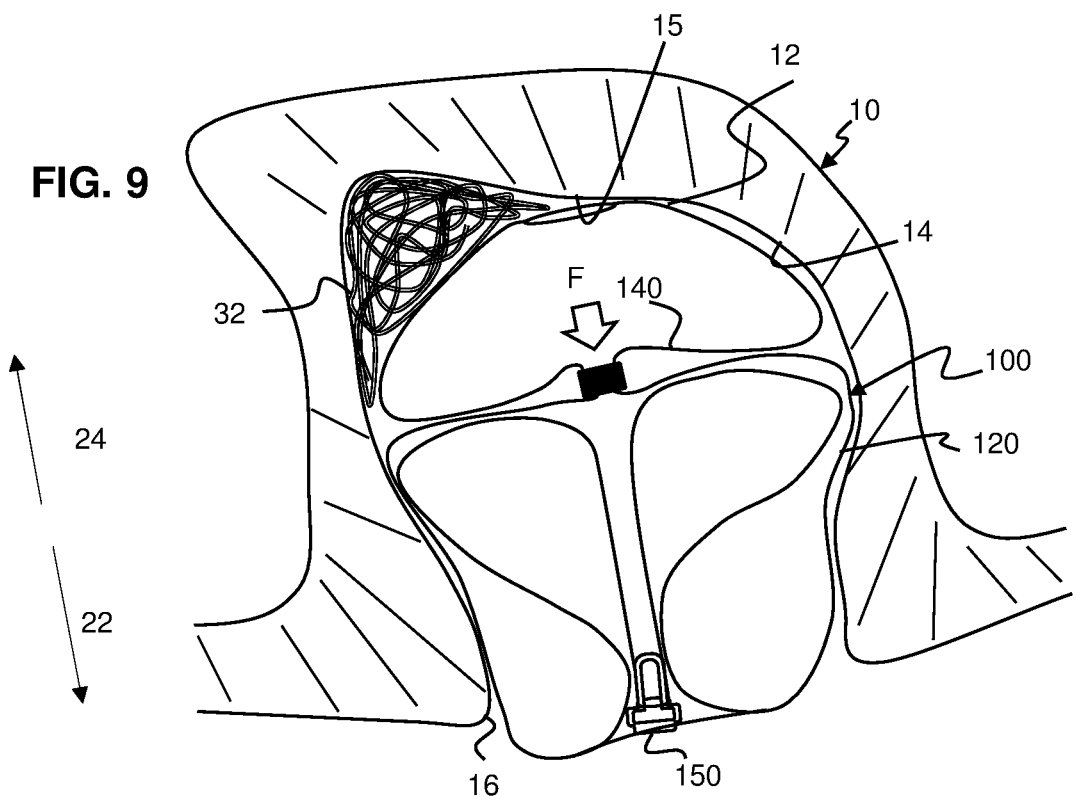
FIG. 9 is an illustration of another aneurysm treatment according to aspects of the present invention.

FIG. 9 is an illustration of another aneurysm treatment. For aneurysms having substantially non-spherical geometry, embolic coils 32 can be implanted prior to the implant 100. The embolic coils 32 can be implanted by known methods. Any of the previously illustrated implants 100, 200, 300, 400 can be subsequently implanted following steps illustrated and described herein and variations thereof.

FIGS. 10A and 10B are illustrations of another example implant 500 in a predetermined shape (FIG. 10A) and an implanted shape (FIG. 10B). The implant 500 includes an embolic coil 552 formed in a spiraling predetermined shape. The embolic coil 552 can function as a dome feature configured to press into aneurysm walls near the aneurysm's dome, distal portion of the aneurysm sac.

FIGS. 11A and 11B are illustrations of another example implant in a predetermined shape (FIG. 11A) and an implanted shape (FIG. 11B). The implant 600 includes a wire frame 654 configured to anchor in an aneurysm dome, thereby functioning as a dome feature.

The implants 500, 600 respectively illustrated in FIGS. 10A, 10B, 11A, and 11B can respectively further include a proximal braided segment 520, 620 configured to extend across the aneurysm neck and anchor to the aneurysm's walls at least in the proximal portion of the aneurysm sac 12. Each of the proximal braided segments 520, 620 can be respectively joined to the embolic coil 552 or wire frame 654 by the band 130. Any of the previously illustrated proximal braided segments 120, 220, 320, 420 and variations thereof can be used in place of either of the proximal braided segments 520, 620 illustrated in FIGS. 10A through 11B. During a treatment, the embolic coil 552 or the wire frame 654 can be elongated within a microcatheter and expelled from the microcatheter into an aneurysm or cavity. The respective proximal braided segment 520, 620 can subsequently be expelled from the catheter and implanted as described elsewhere herein.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%.

The descriptions contained herein are examples of embodiments of the invention and are not intended in any way to limit the scope of the invention. As described herein, the invention contemplates many variations and modifications of the implant and methods of constructing and use the same, including alternative materials, alternative geometries, alternative detachment features, alternative delivery systems, alternative means for forming a braid into a predetermined shape, alternative treatment methods, etc. Variations and modifications that are apparent to a person skilled in the pertinent art are intended to be within the scope of the claims which follow.

What is claimed is:

1. An implant comprising:
   a first braided segment comprising a distal open end;
   a second braided segment comprising a proximal pinched end;
   a band positioned at a junction between the first braided segment and the second braided segment and constricting the first braided segment and the second braided segment at the junction;
   a predetermined shape in which the first braided segment extends in a distal direction from the band forming a bowl shape and the second braided segment extends in a proximal direction from the band and comprises two inversions separating three sections which at least partially overlap each other such that the pinched end is affixed to an innermost section of the three sections, the band is affixed to an outermost section of the three sections, and a middle section of the three sections extends between the two inversions and is positioned within the outermost section and around the innermost section; and wherein a first inversion of the two inversions is a proximal inversion folded toward the distal direction thereby defining the outermost section of the second braided segment, and wherein a second inversion of the two inversions is a distal inversion folded toward the proximal direction thereby defining the middle section.

2. The implant of claim 1, wherein, when the implant is in the predetermined shape, the entirety of the first braided segment is positioned in the distal direction from the entirety of the second braided segment.

3. The implant of claim 1, wherein, when the implant is in the predetermined shape, the band and the pinched end are approximately aligned along a longitudinal axis and the first braided segment and the second braided segment are respectively approximately radially symmetrical with respect to the longitudinal axis.

4. The implant of claim 1 being configured to be manipulated at the pinched end to position the implant in an implanted shape in a spherical cavity, the implanted shape being based in part on the predetermined shape and based in part on the geometry of the spherical cavity.

5. The implant of claim 4, wherein, in the implanted shape, the first braided segment provides a force pressing the second braided segment in the proximal direction due to compression of the first braided section against a dome of the spherical cavity.

6. The implant of claim 4, wherein, in the implanted shape, the open end is positioned approximate a distal wall of the spherical cavity, the band is suspended within the spherical cavity, and the second braided segment comprises the two inversions separating the three sections which at least partially overlap each other.

7. The implant of claim 6, wherein the two inversions and the three sections of the second braided segment when the implant is in the implanted shape correspond approximately to the two inversions and the three sections of the second braided segment when the implant is in the predetermined shape.

8. The implant of claim 4,
   wherein, in the implanted shape, a diameter of the open end is collapsed in comparison to the diameter of the open end when the implant is in the predetermined shape, and
   wherein, in the implanted shape, a height of the first segment is foreshortened in comparison to the height of the first segment when the implant is in the predetermined shape.

9. The implant of claim 1,
   wherein the implant is stable in a first implanted shape based on the predetermined shape when constrained by a first substantially spherical cavity and the implant is stable in a second implanted shape based on the predetermined shape when constrained by a second substantially spherical cavity smaller than the first substantially spherical cavity,
   wherein, in the first implanted shape, the open end is positioned approximate a distal wall of the first substantially spherical cavity, the band is suspended within the first substantially spherical cavity, and the second braided segment comprises two inversions separating three sections which at least partially overlap each other such that the two inversions and the three sections of the second braided segment when the implant is in the first implanted shape correspond approximately to the two inversions and the three sections of the second braided segment when the implant is in the predetermined shape, and
   wherein, in the second implanted shape, the open end is positioned approximate a distal wall of the second substantially spherical cavity, the band is suspended within the second substantially spherical cavity, and the second braided segment comprises two inversions separating three sections which at least partially overlap each other such that one of the two inversions, when the implant is in the second implanted shape, corresponds to a bend in the middle section when the implant is in the predetermined shape.

10. A method for constructing an implant, the method comprising:
    affixing a band at a junction between a first braided segment and a second braided segment, the first braided segment comprising a distal open end and the second braided segment comprising a proximal pinched end; and
    shaping, as follows, the implant to a predetermined shape to which the implant is capable of self-expanding:
       forming the first braided segment to a bowl shape extending in a distal direction from the band;
       inverting the second braided segment to form a proximal inversion folded toward the distal direction thereby defining an outermost section of the second braided segment; and inverting the second braided segment to form a distal inversion folded toward the proximal direction thereby defining a middle section between the proximal and distal inversions of the second braided segment that is at least partially surrounded by the outermost section and defining an innermost section between the distal inversion and the pinched end that is at least partially surrounded by the middle section.

11. The method of claim 10, further comprising:
shaping the implant to the predetermined shape such that when the implant is in the predetermined shape, the entirety of the first braided segment is positioned in the distal direction from the entirety of the second braided segment.

12. The method of claim 10, further comprising:
shaping the implant to the predetermined shape such that when the implant is in the predetermined shape, the band and the pinched end are approximately aligned along a longitudinal axis and the first braided segment and the second braided segment are respectively approximately radially symmetrical with respect to the longitudinal axis.

13. The method of claim 10, further comprising:
collapsing the implant;
positioning the implant in a microcatheter sized to traverse neurovasculature; and
affixing a delivery system to the implant approximate the pinched end so that the pinched end can be manipulated to move the implant from a distal end of the microcatheter.

14. The method of claim 10, further comprising:
forming a bend in the middle section of the second braided segment that is configured to fold to form the distal inversion when the implant is positioned, via manipulation of the pinched end, in a substantially spherical cavity.

15. A method of treating an aneurysm, the method comprising:
pushing an open end of a first braided segment of an implant from a distal end of a microcatheter into a sac of an aneurysm;
positioning the open end near a distal wall of the aneurysm;
shaping the first braided segment to form a distal sack positioned against a dome of the aneurysm and extending centrally through the sac of the aneurysm to a band affixed to a proximal end of the first braided segment and a distal end of a second braided segment;
shaping an outer section of the second braided segment of the implant to form a proximal sack extending centrally through the sac of the aneurysm from the band, positioned against a portion of an aneurysm wall in a proximal direction from the distal sack, and extending across at least a portion of a neck opening of the aneurysm;
inverting the second braided segment approximate the neck opening; and
inverting the second braided segment within the proximal sack,
wherein the implant comprises a predetermined shape in which the second braided segment comprises two inversions separating three sections which at least partially overlap each other such that a pinched end of the second braided segment is affixed to an innermost section of the three sections, the band is affixed to an outermost section of the three sections which forms the proximal sack, a middle section of the three sections extends between the two inversions, the middle section is positioned within the outermost section and around the innermost section, and the middle section comprises a bend,
wherein a first inversion of the two inversions is a proximal inversion folded toward the distal direction thereby defining the outermost section of the second braided segment, and
wherein a second inversion of the two inversions is a distal inversion folded toward the proximal direction thereby defining the middle section.

16. The method of claim 15, further comprising:
pressing the distal sack into the dome.

17. The method of claim 15, further comprising:
implanting embolic coils near the distal wall of the aneurysm; and
pressing the distal sack into the embolic coils.

18. The method of claim 15, further comprising:
releasing the implant in an implanted configuration such that the first braided segment provides a force to press the second braided segment in the proximal direction.

19. The method of claim 15,
wherein inverting the second braided segment within the proximal sack comprises folding the middle section at the bend such that the bend forms the distal inversion of the second braided segment within the proximal sack.

* * * * *